(12) United States Patent
Lee et al.

(10) Patent No.: US 10,731,208 B2
(45) Date of Patent: Aug. 4, 2020

(54) MICROFLUIDIC DEVICE FOR DETECTING TARGET GENE, METHOD FOR MANUFACTURING SAME, AND METHOD FOR DETECTING USING SAME

(71) Applicants: EWHA UNIVERSITY—INDUSTRY COLLABORATION FOUNDATION, Seoul (KR); KOREA ADVANCED INSTITUTE OF SCIENCE AND TECHNOLOGY, Daejeon (KR)

(72) Inventors: Hyukjin Lee, Seoul (KR); Haeshin Lee, Daejeon (KR); Ho Yeon Lee, Daejeon (KR); Il Young Jung, Sejong (KR)

(73) Assignees: EWHA UNIVERSITY—INDUSTRY COLLABORATION FOUNDATION, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 552 days.

(21) Appl. No.: 15/522,812

(22) PCT Filed: Oct. 30, 2015

(86) PCT No.: PCT/KR2015/011605
§ 371 (c)(1),
(2) Date: Apr. 28, 2017

(87) PCT Pub. No.: WO2016/068663
PCT Pub. Date: May 6, 2016

(65) Prior Publication Data
US 2017/0314070 A1    Nov. 2, 2017

(30) Foreign Application Priority Data
Oct. 30, 2014    (KR) ........................ 10-2014-0149495

(51) Int. Cl.
*C12Q 1/6853*    (2018.01)
*B01L 7/00*    (2006.01)
(Continued)

(52) U.S. Cl.
CPC .............. *C12Q 1/6853* (2013.01); *B01L 3/00* (2013.01); *B01L 3/502707* (2013.01);
(Continued)

(58) Field of Classification Search
CPC ... C12Q 1/6853; C12Q 1/68; B01L 3/502707; B01L 3/502715; B01L 3/502761;
(Continued)

(56) References Cited

U.S. PATENT DOCUMENTS 7,695,956 B2    4/2010    Tsinberg et al.
9,458,489 B2    10/2016    Lim et al.
(Continued)

FOREIGN PATENT DOCUMENTS

KR    1020080096661 A    10/2008
KR    1020130000396 A    1/2013
(Continued)

OTHER PUBLICATIONS

Arata et al. (PLOS One Nov. 2012 vol. 7 Issue 11 e48329 (Year: 2012).*
(Continued)

*Primary Examiner* — Sally A Merkling
(74) *Attorney, Agent, or Firm* — Caesar Rivise, PC

(57) ABSTRACT

The present invention provides facile and accurate molecular diagnosis of disease-specific genes capable of the naked eye detection through amplifying the target genes to selectively block the fluid path in a microfluidic device. Specifically, the present invention includes an isothermal amplification of target genes through a rolling circle amplification, a microfluidic device for detecting pathogen genes, and a
(Continued)

detection method using the same. Therefore, the present invention can conveniently detect a single target gene, such as a single pathogen, or at the same time, several target genes, such as several pathogens, without complicated mechanical equipment.

14 Claims, 15 Drawing Sheets

Specification includes a Sequence Listing.

(51) Int. Cl.
  *C12M 1/38* (2006.01)
  *C12Q 1/68* (2018.01)
  *B01L 3/00* (2006.01)
(52) U.S. Cl.
  CPC ... *B01L 3/502715* (2013.01); *B01L 3/502761* (2013.01); *B01L 7/00* (2013.01); *C12M 1/38* (2013.01); *C12Q 1/68* (2013.01); *B01L 2200/12* (2013.01); *B01L 2300/0816* (2013.01); *B01L 2300/0864* (2013.01); *B01L 2300/16* (2013.01); *Y02A 50/451* (2018.01); *Y02A 50/54* (2018.01); *Y02A 50/58* (2018.01)
(58) Field of Classification Search
  CPC ......... B01L 2200/12; B01L 2300/0816; B01L 2300/0864; B01L 2300/16; B01L 3/00; B01L 7/00; B01L 3/5027; B01L 7/52; B01L 2300/0861; Y02A 50/451; Y02A 50/54; Y02A 50/58; C12M 1/38
  See application file for complete search history.

(56) References Cited

U.S. PATENT DOCUMENTS

| | | | | |
|---|---|---|---|---|
| 2003/0198962 | A1* | 10/2003 | Chung | C12Q 1/6832 435/6.12 |
| 2008/0311497 | A1* | 12/2008 | Wu | G03G 5/0609 430/59.5 |
| 2009/0098541 | A1 | 4/2009 | Southern et al. | |
| 2013/0130226 | A1* | 5/2013 | Lim | B01L 3/50273 435/2 |

FOREIGN PATENT DOCUMENTS

| | | |
|---|---|---|
| KR | 1020130066293 A | 6/2013 |
| KR | 1020130135111 A | 12/2013 |
| KR | 101391862 B1 | 5/2014 |

OTHER PUBLICATIONS

Long et al. Biosensors and Bioelectronics 46 (2013) 102-107 (Year: 2013).*
Khatami et al. (Iran Red Crescent Med J 2012; 14(9) 594-598 (Year: 2012).*
English language abstract for KR 101391862 B1 (2014).
English language abstract for KR 1020130066293 A (2013).
English language abstract for KR 1020130135111 A (2013).
International Search Report from corresponding PCT/KR2015/011605 dated Feb. 26, 2016.
Arata et al. (2012). Rapid and sensitive microRNA detection with laminar flow-assisted dendritic amplification on power-free microfluidic chip. Plos One, 7(11) 1-6.
Chang et al. (2012). Diagnostic devices for isothermal nucleic acid amplification. Sensors, 12, 8319-8337.
Lee et al. (2015). DhITACT: DNA hydrogel formation by isothermal amplification of complementary target in fluidic channels. Advanced Materials, 27, 3513-3517.
Stougaard et al. (2011). Strategies for highly sensitive biomarker detection by Rolling Circle Amplification of signals from nucleic acid composed sensors. Integrative Biology, 3, 982-992.
McCarthy et al. (2006). Detection and identification of IHN and ISA viruses by isothermal DNA amplification in microcapillary tubes. Analytical and Bioanalytical Chemistry, 386, 1975-1984.
McCarthy et al. (2007). Nucleic acid sensing by regenerable surface-associated isothermal rolling circle amplification. Biosensors and Bioelectronics, 22, 1236-1244.
Sato et al. (2010). Microbead-based rolling circle amplification in a microchip for sensitive DNA detection. Lab on a Chip, 10, 1262-1266.
Zhou et al. (2010). A dumbbell probe-mediated rolling circle amplification strategy for highly sensitive microRNA detection. Nucleic Acids Research, 38(15), 1-5.

* cited by examiner

MICROFLUIDIC DEVICE FOR DETECTING TARGET GENE, METHOD FOR MANUFACTURING SAME, AND METHOD FOR DETECTING USING SAME

CROSS-REFERENCE TO RELATED APPLICATIONS

This application is the U.S. National Phase Application of PCT/KR2015/011605, filed Oct. 30, 2015, which claims priority from KR 10-2014-0149495, filed Oct. 30, 2014, the contents of which applications are incorporated herein by reference in their entireties for all purposes.

TECHNICAL FIELD

The present invention relates to a diagnostic device for detecting a target gene, a method for manufacturing the same, and a detection method using the same. Specifically, the present invention relates to a microfluidic device for detecting a target gene that detects various pathogens through the detection of disease-specific genes, a method for manufacturing the same, and a detection method using the same.

More specifically, the present invention relates to a microfluidic device for detecting a target gene that is capable of identifying a disease-specific target gene with the naked eye by amplifying the target gene to selectively block a channel of the microfluidic device, a method for manufacturing the same, and a method for detecting a target gene using the same.

The present research has been conducted with the support of the Biomedical Technology Development Program and Basic Science Research Program from the National Research Foundation of Korea funded by the Ministry of Science, ICT and Future Planning of the Republic of Korea and the Health and Medical Technology R&D Project from the Korea Health Industry Development Institute funded by the Ministry of Health and Welfare.

BACKGROUND ART

Various PCR-based methods have been reported as gene detection techniques. A SDT/RT-PCR (simple-direct tube RT-PCR) method directly using PCR and an IC/RT-PCR (Immunocapture RT-PCR) method including an immunologic method to eliminate a PCR reaction inhibitor and to increase sensitivity have been developed to be used for gene detection.

In particular, to initially deal with infectious diseases caused by various bacteria and virus pathogens and to prevent the progression and widespread of the diseases, it is necessary to quickly and accurately diagnose the infection with a specific pathogen. If it is possible to diagnose patients with an infectious pathogen in the latent period before any symptoms appear, the spread of the infection may effectively be prevented to avoid serious social and economic damages.

Methods developed so far involve great time and human resource in culturing and detecting pathogens for diagnosis, have insufficient accuracy in determining infection, need a machine or device requiring external power supply including a thermal cycler, and have difficulty in simultaneously detecting a plurality of pathogens.

In a diagnosis method using a PCR kit, a thermal cycler is essentially required and it is difficult to meet cycling temperature, time, conditions of buffer solutions, and the like in PCR, thus making it difficult to detect multiple pathogens at the same time.

Therefore, it is required to develop a method for conveniently and accurately detecting a target gene, such as a disease-specific target gene with reduced detection costs and time.

Related document: KR Patent Publication No. 2010-0053831

DISCLOSURE OF INVENTION

Technical Goals

The present invention aims to provide a microfluidic device for the diagnosis of a target gene that is capable of conveniently and accurately detecting a target gene in any environment without external power supply or a special device including a thermal cycler, a method for manufacturing the same, and a detection method using the same.

Technical Solutions

To address the foregoing problems, the present invention provides a microfluidic device for detecting a target gene, a method for manufacturing the same, and a detection method using the same. Hereinafter, each invention is described in detail.

Microfluidic Device for Detecting a Target Gene

According to one specific example of the present invention, there is provided a microfluidic device for detecting a target gene including: a board; an inlet which is formed on the board and through which a sample solution is introduced from the outside; a first channel connected to the sample inlet to accommodate the introduced sample solution; a second channel connected to the first channel; an outlet connected to the second channel; a surface coating on the second channel; a primer immobilized on the surface coating of the second channel; and a template complementarily binding to the primer, wherein the template includes a binding region complementary to a target gene, a binding region complementary to the primer, and an in-template complementary binding region to form a dumbbell shape, the binding regions complementary to the target gene are separately formed at both ends of the template, and the binding region complementary to the primer is formed between the in-template complementary binding regions to form the dumbbell shape, which are separately formed.

That is, the microfluidic device for detecting the target gene according to the present invention is a device including a board, an inlet, a first channel, and an outlet connected to a second channel. The second channel of the device has a surface coating, the primer is immobilized on the surface coating, and a template (template for detecting a target gene) binds to the immobilized primer. The template has a linear structure of 'first target gene binding region-first in-template complementary binding region (to form the dumbbell shape)-primer binding region-second in-template complementary binding region (to form the dumbbell shape)-second target gene binding region.' That is, in this structure, the primer binding region of the template binds to the primer immobilized on the device, the 'first target gene binding region-first in-template complementary binding region (to form the dumbbell shape) is present at one end of the primer binding region, and the 'second in-template complementary binding region (to form the dumbbell shape)-second target gene binding region' is present at the other end of the primer binding region.

When target genes are present in a sample, the target genes bind to both the first target gene binding region and the second target gene binding region of the template. Then, the first in-template complementary binding region and the second in-template complementary binding region become physically close to each other to form complementary binding with the target gene. Thus, as seen from B of FIG. 2, the template turns a dumbbell shape having a nick between the first target gene binding region and the second target gene binding region.

That is, the microfluidic device for detecting the target gene according to the present invention is a microfluidic device for detecting a target gene that includes: a board; an inlet which is formed on the board and through which a sample solution is introduced from the outside; a first channel connected to the sample inlet to accommodate the introduced sample solution; a second channel connected to the first channel; and an outlet connected to the second channel, wherein the second channel has a surface coating on the surface; a primer is immobilized on the surface coating; a template for detecting a target gene binds to the immobilized primer; the template for detecting the target gene includes a primer binding region complementary to the primer, a first in-template complementary binding region binding to one end of the primer binding region-first target gene binding region, and a second in-template complementary binding region binding to the other end of the primer binding region-second target gene binding region According to one specific example of the present invention, the second channel may have a shape of being connected to the first channel and dividing into two or more, preferably 2 to 20 branches. The number of branches of the second channel may vary on the number of templates of target genes to be detected for the diagnosis of disease-specific genes. For example, when there are two target gene templates, the number of branches of the second channel may be two, or three including those for the target gene templates and a control group. For example, when there is one target gene template, the number of branches of the second channel may be one, or two including those for the target gene template and a control group.

The number of sample outlets may be the same as the number of branches of the second channel. For example, the number of sample outlets may be two or more, preferably 2 to 20, the same as the number of branches of the second channel.

According to one specific example of the present invention, to ease immobilization of the primer on the second channel, the second channel may be coated to have a functional group to combine with the primer. Also, the primer may be modified to have a functional group to combine with the functional group on the second channel.

According to one specific example of the present invention, the second channel of the microfluidic device according to the present invention may be coated with pyrogallol amine, for example, 5-hydroxydopamine HC1.

One end of the primer may be modified to have various functional groups, for example, one or more selected from the group consisting of thiol, amine, hydroxyl, carboxyl, isothiocyanate, NHS ester, aldehyde, epoxide, carbonate, HOBt ester, glutaraldehyde, carbamate, imidazole carbamate, maleimide, aziridine, sulfone, vinylsulfone, hydrazine, phenyl azide, benzophenone, anthraquinone, and diene.

In one embodiment of the present invention, the coating of the second channel may be 5-hydroxydopamine HCl, and one end of the primer may be modified into a thiol or amine group.

According to one specific example of the present invention, the template may be designed to have various lengths and sequences in view of the length of a target gene, for example, a pathogen gene, and the length of a primer. According to one specific example of the present invention, the template may have a length of 40 to 160 mer. In the present invention, when the template is too short, the template is unstable; when the template is too long, rolling circle amplification (RCA) efficiency may be reduced.

According to one specific example of the present invention, in the template, binding regions complementary to a pathogen gene are separately formed at both ends of the template, in-template complementary binding regions to form a dumbbell shape are separately formed to be adjacent to the binding regions complementary to the pathogen gene at both ends, and a primer binding region complementary to the primer is formed between the in-plate complementary binding regions to form the dumbbell shape (see A of FIG. 2).

According to one specific example of the present invention, the template may be a template with a total length of 40 to 160 mer including the 10 to 40 mer-long binding regions complementary to the target gene, the 10 to 40 mer-long binding region complementary to the primer, and the 20 to 80 mer-long in-template complementary binding regions complementary to form the dumbbell shape.

According to one specific example of the present invention, the sample solution introduced into the microfluidic device for detecting the target gene may be a body fluid sample, such as blood, salvia and urine, food, a water supply source, and various sample solutions, such as water or soil samples, for analyzing water contamination, soil contamination, or the like.

Further, a solution of only nucleic acids extracted from various sample solutions may be introduced into the microfluidic device for detecting the target gene. Here, extraction is not limited to a specified method but may be performed by a liquid-liquid extraction method, such as a phenol-chloroform extraction, or a solid-liquid extraction method using a carrier. Further, extraction may use a proteinase K/phenol extraction, a proteinase K/phenol/chloroform extraction, alkaline lysis, an alkaline-SDS method, or a bacteriolytic enzyme method. In addition, a commercially available nucleic acid extraction method, QIAamp (manufactured by QIAGEN, Germany), may be used. For example, phenol and a phenol/chloroform mixture may be used.

In the present invention, the target gene, for example, a nucleic acid sequence or molecule, may be single- or double-stranded or may be a sense or antisense strand of DNA or RNA. Thus, the nucleic acid sequence may be dsDNA, ssDNA, mixed ssDNA, mixed dsDNA, dsDNA made of ssDNA (for example, using fusion, modification, a helicase, or the like), A-, B-, or Z-DNA, triple-stranded DNA, RNA, ssRNA, dsRNA, mixed ssRNA and dsRNA, dsRNA made of ssRNA (for example, using fusion, modification, a helicase, or the like), messenger RNA (mRNA), ribosome RNA (rRNA), transfer RNA (tRNA), catalytic RNA, snRNA, microRNA, or protein-nucleic acid (PNA).

The present invention is not limited by the type or supply source of a used target gene, for example, a nucleic acid (for example, a sequence or molecule (for example, target sequence and/or oligonucleotides)). When used in relation to a nucleic acid sequence, the terms "nucleotide" and "base" are replaced with each other unless specified otherwise in the present specification.

The present invention also provides a microfluidic device kit for detecting a target gene including: the microfluidic device for detecting the target gene; a dNTP; a ligase; and an isothermal nucleic acid polymerase.

In the kit, the dNTP, the ligase, and the isothermal nucleic acid polymerase may be included in an amplification composition for amplifying a gene product (nucleic acid). The amplification composition refers to a mixture containing all components for amplifying a nucleic acid and may further include a nucleic acid polymerase (enzyme), a buffer solution necessary for the activation or reaction of the nucleic acid polymerase, four kinds of dNTPs, a cofactor, and/or a substrate. The nucleic acid polymerase may be a DNA polymerase, an RNA polymerase, a reverse transcriptase, and a combination thereof.

According to one specific example of the present invention, the amplification composition provides a nucleic acid amplifying composition including a DNA polymerase, a reaction buffer solution, and dNTPs.

According to one specific example of the present invention, the DNA polymerase may be selected from the group consisting of *E. Coli* DNA polymerase I, Klenow Fragment, phi29 DNA polymerase, Vent DNA polymerase, T4, T7 DNA polymerase, and Taq polymerase.

According to one specific example of the present invention, the buffer solution (buffer) may be New England Biolabs (NEB) buffer solutions, for example, MEB buffer solution 4, Bst DNA polymerase buffer solution, T4 DNA ligase buffer solution, T7 DNA ligase buffer solution, and the like, without being limited thereto.

According to one specific example of the present invention, the microfluidic device for detecting the target gene may further include a detection composition to detect the hydrogel formation of amplified gene products detected by the microfluidic device or a change in turbidity.

Further, the detection composition may be a dye reagent to aid the naked-eye identification of an amplified gene product, which may exhibit a color and includes, for example, GelRed, Streptavidin beads, trypan blue dye, Evans blue dye, hematoxylin-eosin stain, crystal violet, or methylene blue, without being limited thereto.

Moreover, the detection composition may be a high salt solution, which increases flocculation of amplified gene products to cause a change in turbidity or precipitation, thus aiding the naked-eye identification of the amplified gene products. The high salt solution may be an inorganic salt solution, for example, an aqueous magnesium chloride ($MgCl_2$) solution, an aqueous ammonium chloride ($NH_4Cl$) solution, an aqueous ammonium acetate ($NH_4OA_C$) solution, an aqueous sodium chloride (NaCl) solution, an aqueous ammonium sulfate (($NH_4)_2SO_4$) solution, or an aqueous solution containing a neutral amino acid solution, without being limited thereto.

In addition, the detection composition may be a fluorescent reagent.

According to one specific example of the present invention, the second channel of the device may be of such diameter that amplified gene products (mass) flocculate to block the second channel. The second channel may have a diameter of 1 µm to 5 mm in one specific example, and may have a diameter of 50 µm to 5 mm in another specific example. Alternatively, the second channel may have a diameter of 0.25 mm to 2 mm in one specific example, and may have a diameter of 0.5 mm to 1.5 mm in another specific example.

According to one specific example of the present invention, the amplified gene products (mass) may have a diameter of about 0.5 µm to about 50 µm. In one specific example of the present invention, the amplified gene products (mass) may flocculate to form hydrogel, thus having a diameter of about 50 µm to 5 mm. In another specific example of the present invention, the amplified gene products may flocculate to have a diameter of about 0.25 mm to 2 mm.

According to one specific example of the present invention, the surface of the second channel of the microfluidic device may include any one of polydimethylsiloxane, gold (Au), metal oxides ($SiO_2$, $TiO_2$, $Al_2O_3$, and indium-tin oxide), ceramic, and synthetic polymers (polycarbonate, a cyclic olefin copolymer, polytetrafluoroethylene (PTFE), polystyrene, and polyethylene).

According to one specific example of the present invention, the coating material may include a hydroxybenzene monomer or polymer coating. Further, the coating material may include, for example, a catecholamine polymer coating. Hydroxybenzene monomers or polymers have excellent surface properties and thus may easily coat a wide range of materials including precious metals, metal oxides, ceramic, and synthetic polymers. Specific examples of the hydroxybenzene monomers and polymers may unrestrictedly include dopamine, 5-hydroxydopamine HCl, norepinephrine, epinephrine, pyrogallol amine, 3,4-Dihydroxyphenylalanine, catechin, tannins, pyrogallol, pyrocatechol, heparin-catechol, chitosan-catechol, poly(ethylene glycol)-catechol, poly(ethyleneimine)-catechol, poly(methyl methacrylate)-catechol, and hyaluronic acid-catechol.

Further, the coating material may be a vinyl group.

There is no restriction on coating methods. For example, a coating composition may be prepared and may be put into the second channel to coat the surface of the second channel. For another example, the second channel may be coated with a vinyl group coating by vapor deposition.

According to one specific example of the present invention, the microfluidic device of the present invention enables the identification of amplified gene products of a target gene with the naked eye. In one specific example of the present invention, such detection may be identified with the naked eye as the amplified gene products flocculate to form hydrogel or turbidity is changed.

According to one specific example of the present invention, a target gene to be detected may be obtained from an animal, a plant, bacteria, a virus, or a fungus. Preferably, the target gene may be obtained from a pathogen, such as bacteria, a virus or a fungus.

According to one specific example of the present invention, the target gene to be detected may be a pathogen gene. The target gene may be all pathogens with a known nucleic acid sequence. According to one specific example of the present invention, the pathogens are useful to detect avian influenza, SARS, *Escherichia coli* O157:H7, *Mycobacterium tuberculosis, Bacillus anthracis, Streptococcus pneumonia, Plasmodium, Salmonella,* Hepatitis A,B,C,D and E virus, *Francisella tularensis, Yersinia pestis, Yersinia enterocolitica* and Ebola virus, and MERS-Cov virus. Further, according to one specific example of the present invention, the pathogens are also useful to detect a pathogen having antibiotic resistance, such as *Streptococcus pneumonia, enterococcus, staphylococcus, Plasmodium falciparum*, and tuberculosis or malaria bacteria in developing countries.

Table 1 below illustrates detectable the kinds and sequences of detectable target genes, for example, pathogens, and the sequences of templates including binding regions complementary thereto according to one specific example of the present invention (bold font: binding region complementary to target pathogen gene, italic font: in-template complementary region, underlined italic font: binding region complementary to primer).

TABLE 1

| Pathogen kind | SEQ ID NO; | Template sequence (5'→3') | SEQ ID NO: | Target gene sequence of pathogen |
|---|---|---|---|---|
| Salmonella | 1 | 5'-phosphate-TG CTA TGC CGA CTC AAT CGA AGT ACT CAG CGT AAG TTT AGA GGC AT <u>TA GCA TGC TAG TAT CGA CGT CCC</u> ACG TAC CAA CAA CTT ACG CTG AGT ACT TCG ATT TG AGT G-3' | 5 | 5'-GAG TCG GCA TAG CAC ACT CA-phosphate-3' |
| Yersinia enterocolitica | 2 | 5'-phosphate-GC TCA CCC CAG TAA AAT CGA AGT ACT CAG CGT AAG TTT AGA GGC AT <u>TA GCA TGC TAG TAT CGA CGT CCC</u> ACG TAC CAA CAA CTT ACG CTG AGT ACT TCG ATT AG CTT TAC-3' | 6 | 5'-TTA CTG GGG TGA GCG TAA AGC T-phosphate-3' |
| Francisella tularensis | 3 | 5'-phosphate-TG TTT CCA GTA TTT AAT CGA AGT ACT CAG CGT AAG TTT AGA GGC AT T<u>A GCA TGC TAG TAT CGA CGT CCC</u> ACG TAC CAA CAA CTT ACG CTG AGT ACT TCG ATT TTT CCT CCG A-3' | 7 | 5'-AAA TAC TGG AAA CAT CGG AGG AAA-phosphate-3' |
| Yersinia pestis | 4 | 5'-phosphate-TC GAA TGC CAA CAA AAT CGA AGT ACT CAG CGT AAG TTT AGA GGC AT <u>TA GCA TGC TAG TAT CGA CGT CCC</u> ACG TAC CAA CAA CTT ACG CTG AGT ACT TCG ATT CTC TGA ACA-3' | 8 | 5'-TTG TTG GCA TTC GAT GTT CAG AG-phosphate-3' |

In this case, as a primer, a binding form complementary to the template sequences, 5'-Thiol-AAA AAA AAA GGG ACG TCG ATA CTA GCA TGC TA 3' (SEQ ID NO:9), may be used.

Table 2 below illustrates detectable the kinds and sequences of detectable target genes, for example, pathogens, and the sequences of templates including binding regions complementary thereto according to Example 3 of the present invention.

TABLE 2

| Pathogen kind | SEQ ID NO: | Template sequence (5'→3') | SEQ ID NO: | Target gene sequence of pathogen |
|---|---|---|---|---|
| Bacillus anthracis | 10 | 5'-phosphate TTT GAA ATG GAG AAA ATC GAA GTA CTC AGC GTA AGT TTA GAG GTA GCA TGC TAG TAT CGA CGT ACG TAC CAA CTT ACG CTG AGT ACT TCG ATT TGA GCG-3' | 12 | 5'-TTC TCC ATT TCA AAC GCT CA phosphate-3' |
| Ebola virus | 11 | 5'-phosphate GA CGC ACG CG A ATC GAA GTA CTC AGC GTA AGT TTA GAG GTA GCA TGC TAG TAT CGA CGT ACG TAC CAA CTT ACG CTG A GT ACT TCG ATT AAC GAG AAA TCG CAC-3' | 13 | 5'-CGC GTG CGT CGT GCG ATT TCT CGT T-phosphate-3' |

Table 3 below illustrates detectable the target gene sequence of detectable MERS-CoV, and the sequence of a template including a binding region complementary thereto according to Example 5 of the present invention.

TABLE 3

| Pathogen kind | SEQ ID NO: | Template sequence (5'→3') | SEQ ID NO: | Target gene sequence of pathogen |
|---|---|---|---|---|
| MERS-CoV | 16 | 5'-5phosphate/AGG GCA CAT CTC CGA ATC GAA GTA CTC AGC GTA AGT TTA GAG GTA GCA TGC TAG TAT CGA CGT ACG TAC CAA CTT ACG CTG AGT ACT TCG ATT ATA CCC 3' | 17 | 5'-CG GAG AUG UGC CCU GGG UAU/3phosphate-3' |

The microfluidic device for detecting the target gene according to the present invention may any kind of pathogens, without being limited to the aforementioned. A random pathogen sequence is selected from known pathogen genes, and two sequences capable of binding to the pathogen sequence with a nick interposed therebetween are prepared to be used as target gene binding region sequences of a template (first target gene binding region and second target gene binding region). In this manner, by replacing only target gene binding region sequences of a template, a target gene-detecting microfluidic device that is capable of detecting a wide variety of pathogen genes may be manufactured.

Although the microfluidic device for detecting the target gene according to the present invention sufficiently enables the identification of a pathogen even with the naked eye, those skilled in the art to which the present invention pertains may carry out the present invention in various specific forms depending on purposes, without changing the essential features of the present invention. For instance, those skilled in the art may implement the present invention by further including an electrochemical sensor measuring a current, a voltage, a potential difference, and a resistance change between electrodes, an optical sensor using various light sources, such as ultraviolet rays, visible light, fluorescence, infrared rays, and Raman light source, a nano-sensor using metal, ceramic, and polymer materials, or a biosensor using bio-sensitive materials, such as enzymes, antigens, and antibodies, depending on purposed in order to increase the detection sensitivity of the microfluidic device for detecting the target gene according to the present invention.

Method for Manufacturing Microfluidic Device

A method for manufacturing a microfluidic device for detecting a target gene according to the present invention may include the following operations:

(S1) providing a microfluidic device including a board, an inlet which is formed on the board and through which a sample solution is introduced from the outside, a first channel connected to the inlet to accommodate the introduced sample solution, a second channel connected to the first channel, and an outlet connected to the second channel;

(S2) coating the surface of the second channel of the microfluidic device;

(S3) immobilizing a primer to bind to a template on the coated second channel; and (S4) binding, to the primer, a template including a binding region complementary to a target gene, a binding region complementary to the primer, and an in-template complementary binding region to form a dumbbell shape.

Here, the binding regions complementary to the target gene are separately formed at both ends of the template, and the binding region complementary to the primer is formed between the in-template complementary binding regions to form the dumbbell shape, which are separately formed.

According to one specific example of the present invention, the surface of the second channel of the microfluidic device may include any one of polydimethylsiloxane, gold (Au), metal oxides ($SiO_2$, $TiO_2$, $Al_2O_3$, and indium-tin oxide), ceramic, and synthetic polymers (polycarbonate, a cyclic olefin copolymer, polytetrafluoroethylene (PTFE), polystyrene, and polyethylene).

According to one specific example of the present invention, in the (S2) coating of the second channel of the microfluidic device, a coating material of the second channel may be coated with a hydrophilic material to aid water droplets in moving and may be various materials having a functional group to immobilize the primer on the second channel. According to one specific example of the present invention, to ease immobilization of the primer on the second channel, the second channel may be surface-coated to have a functional group to combine with the primer. Also, the primer may be modified to have a functional group to combine with the functional group on the second channel.

According to one specific example of the present invention, the coating material of the second channel may include a hydroxybenzene monomer or polymer coating. Further, the coating material may include, for example, a catecholamine polymer coating. Hydroxybenzene monomers or polymers have excellent surface properties and thus may easily coat a wide range of materials including precious metals, metal oxides, ceramic, and synthetic polymers. Specific examples of the hydroxybenzene monomers and polymers may unrestrictedly include dopamine, 5-hydroxydopamine HCl, norepinephrine, epinephrine, pyrogallol amine, 3,4-Dihydroxyphenylalanine, catechin, tannins, pyrogallol, pyrocatechol, heparin-catechol, chitosan-catechol, poly(ethylene glycol)-catechol, poly(ethyleneimine)-catechol, poly(methyl methacrylate)-catechol, and hyaluronic acid-catechol. Further, a vinyl group may also be used for coating.

According to one specific example of the present invention, the second channel of the microfluidic device according to the present invention may be coated with pyrogallol amine, for example, 5-hydroxydopamine HCl.

Detection Method for Detecting a Pathogen Gene using Microfluidic Device

A method for detecting a target gene using a microfluidic device for detecting a target gene according to the present invention may include the following operations:

(S1) providing a microfluidic device for detecting a target gene;

(S2) introducing a sample solution into a first channel; and (S3) adding a dNTP, a ligase, and an isothermal nucleic acid polymerase to a second channel of the microfluidic device for detecting the target gene.

According to one specific example of the present invention, the method may further include (S4) allowing amplified gene products to flocculate to form hydrogel with a diameter of 50 μm to 5 mm on the second channel and an outlet.

According to one specific example of the present invention, the template may be designed to have various lengths and sequences in view of the length of a pathogen gene, and the length of a primer. According to one specific example of the present invention, the template may have a length of 40 to 160 mer. In the present invention, when the template is too short, the template is unstable; when the template is too long, RCA efficiency may be reduced.

In the present invention, a primer refers to both a primer to immobilize a template on the second channel and a primer as an initiating material to amplify a gene.

According to one specific example of the present invention, the template of the microfluidic device for detecting the target gene may form a dumbbell shape.

According to one specific example of the present invention, in (S3), when the dNTP, the ligase, and the isothermal nucleic acid polymerase are added, rolling circle amplification (RCA) occurs in the presence of a target gene in the sample solution. That is, when a target gene binds to a binding region complementary to the target gene of the template, the template forms a dumbbell shape and amplification may occur by the isothermal nucleic acid polymerase. The RCA may occur at room temperature, for example, 15° C. to 35° C., preferably 25° C. to 35° C., and 30° C. in one embodiment.

According to one specific example of the present invention, an amplified product resulting from the RCA may be a round-shaped tangled single-strand RCA product having three legs.

According to one specific example of the present invention, the amplified gene may form a tangled single-strand gene product. Referring to FIG. 2, the amplified target gene product may form a successive Velcro-shaped tangled single strand having a hook-shaped round portion and a length. The length may be 0.5 μm to 50 μm. The entirely amplified target gene product may have a tripod shape having round portions and legs with a length.

According to one specific example of the present invention, the tangled single-strand product may form hydrogel.

Further, amplification by the RCA and the reaction of hydrogel formation may occur for three hours or longer, and reaction time may be three hours in one embodiment.

According to another specific example of the present invention, the method may further include (S5) adding a dye reagent, a high salt solution, or a fluorescent reagent.

According to one specific example of the present invention, the dye reagent, the high salt solution, or the fluorescent reagent may serve to ease detection and may be any one of GelRed, Streptavidin beads, trypan blue dye, Evans blue dye, hematoxylin-eosin stain, crystal violet, methylene blue, an aqueous magnesium chloride ($MgCl_2$) solution, an aqueous ammonium chloride ($NH_4Cl$) solution, an aqueous ammonium acetate ($NH_4OA_C$) solution, an aqueous sodium chloride (NaCl) solution, an aqueous ammonium sulfate (($NH_4)_2SO_4$) solution, and a neutral amino acid solution. For example, a dye reagent, GelRed or Streptavidin beads strongly binding to biotin, may be used. Further, the detection composition may be a high salt solution, such as $MgCl_2$ and $NH_4Cl$.

According to one specific example of the present invention, a sample solution to be detected may be loaded on the sample inlet and may flow through the first channel and the second channel.

Effects of Invention

The present invention enables convenient detection of a single target gene, such as a single pathogen, or a plurality of target genes, such as a plurality of pathogens, at the same time at room temperature without any special device and without being affected by external light sources and electric energy.

Therefore, the present invention provides time and cost-effectiveness in manufacturing a device for detecting a pathogen, makes it possible to carry the device, and enables a quick diagnosis without expensive detection equipment.

Accordingly, the present invention enables not only diagnosis of pathogens, such as tuberculosis or malaria in developing countries, or diagnosis of various infectious diseases (for example, Ebola virus and MERS virus) threatening the world but also quick and convenient detection of pathogens related to bioterrorism and environmental pollution, thus having high practical applicability.

BRIEF DESCRIPTION OF DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
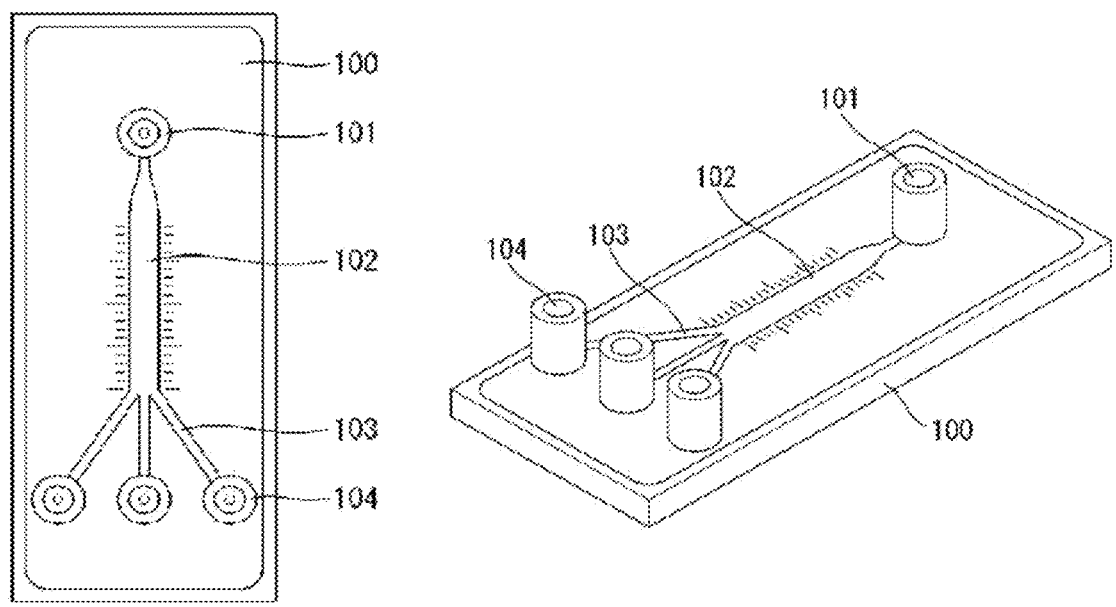
FIG. 1 illustrates a plan view (left) and a perspective view (right) of a microfluidic device for detecting a target gene according to the present invention.

Hereinafter, embodiments are described in detail with reference to the drawings in order to aid the understanding of the present invention. The following embodiments, however, are provided only to illustrate the present invention, and the scope of the present invention should not be limited to the following embodiments and may include different embodiments. In the drawings, the widths, lengths, and thicknesses of elements may be exaggerated for clarity. Like reference numerals refer to like elements throughout the specification. Further, it will be understood that when an element is referred to as being on another element, the element may be directly on another element or an intervening element.

<Preparative Embodiment 1> Manufacture of Template (1) Manufacture of Template_BA A *Bacillus anthracis*-specific template (Template_BA), which is a template specifically binding to *Bacillus anthracis* (Template_BA, SEQ ID NO:10), was manufactured based on the pathogen gene sequence of *Bacillus anthracis* (Integrated DNA Technology, San Jose, Calif., USA). Template_BA includes: binding regions complementary to a target gene (pathogen gene of *Bacillus anthracis*), which are pathogen complementary sites (20 mer, bold letters in a white background); in-template complementary binding regions to form a dumbbell shape, which are in-template complementary regions (21 mer×2, 42 mer in total, italic); and a binding region complementary to a primer, which is a primer immobilization region (37 mer), wherein the binding region complementary to the primer is indicated in underlined italic type.

5'/5Phos/TTT GAA ATG GAG AAA ATC GAA GTA CTC AGC GTA AGT TTA GAG G*TA GCA TGC TAG TAT CGA CGT* ACG TAC CAA CTT ACG CTG AGT ACT TCG ATT TGA GCG-3'

(2) Manufacture of Template_E

A Ebola virus s-specific template (Template_E), which is a template specifically binding to Ebola virus (Template_E, SEQ ID NO:11), was manufactured based on the pathogen gene sequence of Ebola virus. Template_E includes: binding regions complementary to a target gene (pathogen gene of Ebola virus), which are pathogen complementary sites (25 mer, bold letters in a white background); in-template complementary binding regions to form a dumbbell shape, which are in-template complementary regions (21 mer×2, 42 mer in total, italic); and a binding region complementary to a primer, which is a primer immobilization region (37 mer), wherein the binding region complementary to the primer is indicated in underlined italic type.

5'/5Phos/GA CGC ACG CG A ATC GAA GTA CTC AGC GTA AGT TTA GAG G*TA GCA TGC TAG TAT CGA CGT* ACG TAC CAA CTT ACG CTG A GT ACT TCG ATT AAC GAG AAA TCG CAC-3'

<Embodiment 1> Microfluidic Device for Detecting Target Gene

An illustrative configuration of a microfluidic device for detecting a target gene according to the present invention is described with reference to FIGS. 1 to 3.

Figure 2:
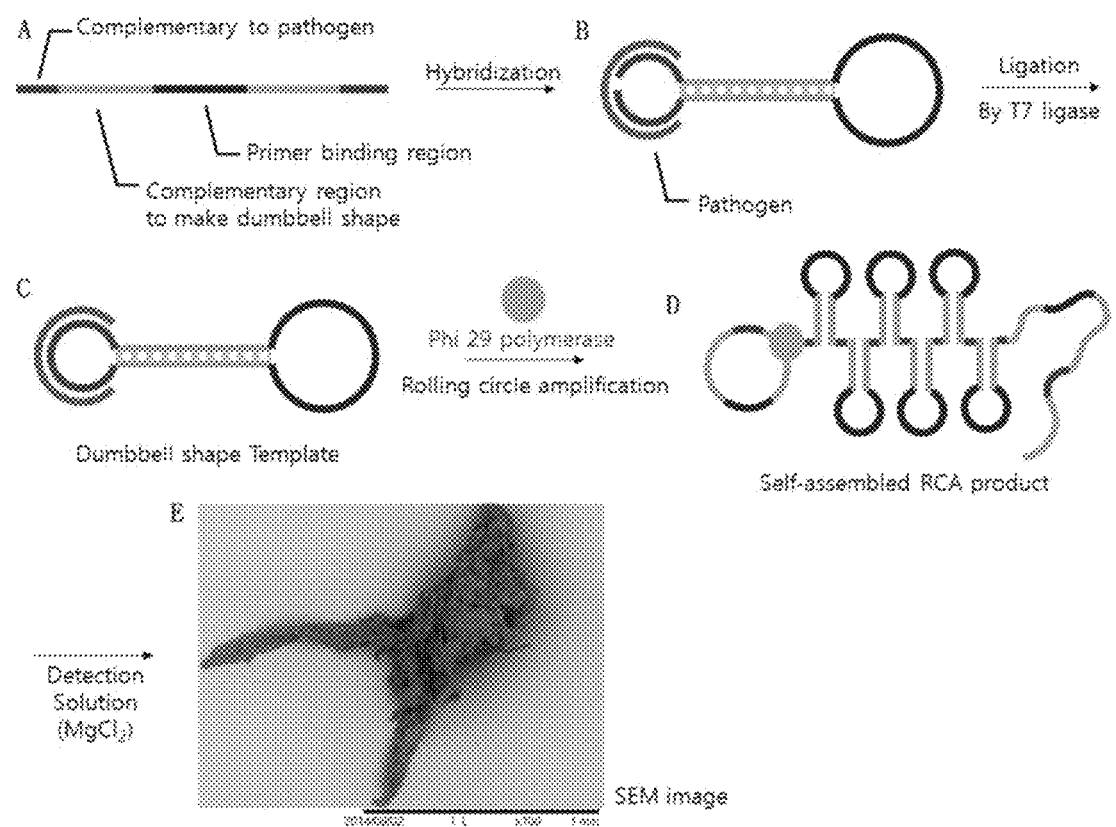
FIG. 2 illustrates a process of detecting a target gene using a dumbbell forming template for detecting the target gene according to the present invention. A, B, C, D, and E each represent an operation of the process.

Referring to FIG. 1, the microfluidic device for detecting the target gene according to the present invention includes: a board 100; an inlet 101 which is formed on the board and through which a sample solution is introduced from the outside; a first channel 102 connected to the inlet to accommodate the introduced sample solution; a second channel 103 connected to the first channel; and an outlet 104 connected to the second channel. The second channel 103 is connected to the first channel and may divide into two or more branches (for example, three branches). Referring to FIG. 3, the microfluidic device for detecting the target gene according to the present invention includes a primer immobilized on the second channel; and a template complementary to the primer. Referring to FIG. 2, the template includes a binding region complementary to a target gene (for example, complementary to a pathogen), a binding region complementary to the primer (primer binding region), and an in-template complementary binding region to form a dumbbell shape (dumbbell shape template). Further, the binding regions complementary to the target gene are separately formed at both ends of the template, and the binding region complementary to the primer is formed between the in-template complementary binding regions to form the dumbbell shape, which are separately formed. That is, as illustrated in A of FIG. 2, the template has a linear structure of 'first target gene binding region-first in-template complementary binding region-primer binding region-second in-template complementary binding region-second target gene binding region.' As illustrated in A of FIG. 12, the primer binding region of the template complimentarily binds to the primer immobilized on the second channel.

To ease immobilization of the primer on the second channel, the second channel may be coated to have a functional group to combine with the primer. Also, the primer may be modified to have a functional group to combine with the functional group on the second channel.

<Embodiment 2> Manufacture of Microfluidic Device for Detecting Target Gene (Device for Detecting Pathogen Gene)

Embodiment 2-1: Method for Manufacturing Microfluidic Device for Detecting Single Target Gene (Method for Manufacturing Microfluidic Device for Detecting Single Pathogen (*Bacillus anthracis*) Gene Operation 1: Operation of Providing Microfluidic Device According to one embodiment of the present invention, a microfluidic device (1 III$^{3in1}$ uncoated Microscopy Chamber (ibidi)) was prepared to manufacture a microfluidic device for detecting a target gene (microfluidic device for detecting a pathogen gene). The microfluidic device of the present invention includes a board 100; an inlet 101 which is formed on the board and through which a sample solution is introduced from the outside; a first channel 102 connected to the inlet to accommodate the introduced sample solution; a second channel 103 connected to the first channel; and an outlet 104 connected to the second channel (see FIG. 1). The second channel 103 may be connected to the first channel and may divide into two or more branches (for example, three branches).

Operation 2: Operation of Coating Second Channel of Microfluidic Device 1 mg/ml of 5-hydroxydopamine HCl (Sigma Aldrich) was dissolved in a 10 mM Tris buffer (1M UltraPure 1M Tris-HCl, pH 8.0, Invitrogen). Next, the pH of the resulting product was adjusted to 8, thereby preparing a coating composition. The second channel of the device (1 III$^{3in1}$ uncoated Microscopy Chamber (ibidi)) was filled with the coating composition. After two hours, the second channel was washed using DDW (Water Purification System, LABOGENE).

Operation 3: Operation of Immobilizing (Combining) Primer Binding to Template on Coated Second Channel Primer-5SS-polyA9 (BIONEER, SEQ ID NO:9) was used as a primer.

After preparing 100 pmol of the primer and 5M DTT (DL-Dithiothreitol, Sigma Aldrich), 100 pmol of the primer and 5 µl of 5 M DTT were mixed, and DDW (Water Purification System, LABOGENE) was added thereto to 50 µl in total. The mixture was subjected to DDT processing for four hours to break a disulfide bond of the primer, after which remaining DTT was eliminated using a 3K Amicon tube (Amicon Ultra Centrifugal Filters 3K, MILLIPORE) (Eppendorf Centrifuge 5415R) (centrifugation was performed twice in total in order to thoroughly eliminate DTT, including first centrifugation for 25 minutes at 132,000 rpm and 4° C. and second centrifugation for 25 minutes at 132,000 rpm and 4° C. with addition of 40 µl of DDW). 5 µl of the solution obtained by eliminating DTT was put into each of the three branches of the second channel 103 (channel 1: the left branch of the second channel of FIG. 1, channel 2: the middle branch of the second channel of FIG. 1, and channel 3: the right branch of the second channel of FIG. 1) and was left for two hours, followed by washing with DDW (Water Purification System, LABOGENE).

Operation 4: Operation of Combining Template Including Binding Region Complementary to Target Gene, Binding Region Complementary to Primer, and In-Template Complementary Binding Region to Form Dumbbell Shape with Primer (Primer-template Combining Operation)

Referring to FIG. 1, a template was applied to the second channel 103 through each outlet 104, thereby combining and fixing each template with the primer immobilized on the second channel 103 having the branches. For a negative control, no template was applied to the second channel. Specifically, a template for *Bacillus anthracis* (Template_B_A, SEQ ID NO:10) was applied to channel 2 of the second channel having the three branches (the middle branch of the second channel of FIG. 1), and channel 1 and channel 3 were used as negative controls. Specifically, 1×PBS (Gibco by Life Technologies) was added to 0.2 µl (=20 pmole) of 100Template_B_A to 5 µl and was put into channel 2, while 6 µl of 1×PBS (Gibco by Life Technoligies) was put into channel 1 and channel 3. After being left for two hours, the second channel was washed with DDW (Water Purification System/LABOGENE).

Embodiment 2-2: Method for Manufacturing Microfluidic Device for Detecting Two or More Target Genes (Method for Manufacturing Microfluidic Device for Detecting Two or More Pathogen (*Bacillus anthracis* and Ebola Virus) Genes Operation 1: Operation of Providing Microfluidic Device According to one embodiment of the present invention, a microfluidic device (1 III$^{3in1}$ uncoated Microscopy Chamber (ibidi)) was prepared to manufacture a microfluidic device for detecting a target gene (microfluidic device for detecting a pathogen gene). The microfluidic device of the present invention includes a board 100; an inlet 101 which is formed on the board and through which a sample solution is introduced from the outside; a first channel 102 connected to the inlet to accommodate the introduced sample solution; a second channel 103 connected to the first channel; and an outlet 104 connected to the second channel (see FIG. 1). The second channel 103 may be connected to the first channel and may divide into two or more branches (for example, three branches).

Operation 2: Operation of Coating Second Channel of Microfluidic Device 1 mg/ml of 5-hydroxydopamine HCl (Sigma Aldrich) was dissolved in a 10 mM Tris buffer (1M UltraPure 1M Tris-HCl, pH 8.0, Invitrogen). Next, the pH of the resulting product was adjusted to 8, thereby preparing a coating composition. The second channel of the device (1 III$^{3in1}$ uncoated Microscopy Chamber (ibidi)) was filled with the coating composition. After two hours, the second channel was washed using DDW (Water Purification System, LABOGENE).

Operation 3: Operation of Immobilizing (combining) Primer Binding to Template on Coated Second Channel Primer-5SS-polyA9 (BIONEER, SEQ ID NO:9) was used as a primer.

After preparing 100 pmol of the primer and 5M DTT (DL-Dithiothreitol, Sigma Aldrich), 100 pmol of the primer and 5 µl of 5 M DTT were mixed, and DDW (Water Purification System, LABOGENE) was added thereto to 50 µl in total. The mixture was subjected to DDT processing for four hours to break a disulfide bond of the primer, after which remaining DTT was eliminated using a 3K Amicon tube (Amicon Ultra Centrifugal Filters 3K, MILLIPORE) (Eppendorf Centrifuge 5415R) (centrifugation was performed twice in total in order to thoroughly eliminate DTT, including first centrifugation for 25 minutes at 132,000 rpm and 4° C. and second centrifugation for 25 minutes at 132,000 rpm and 4° C. with addition of 40 µl of DDW). 5 µl of the solution obtained by eliminating DTT was put into each of the three branches of the second channel 103 (channel 1: the left branch of the second channel of FIG. 1, channel 2: the middle branch of the second channel of FIG. 1, and channel 3: the right branch of the second channel of FIG. 1) and was left for two hours, followed by washing with DDW (Water Purification System, LABOGENE).

Figure 3:
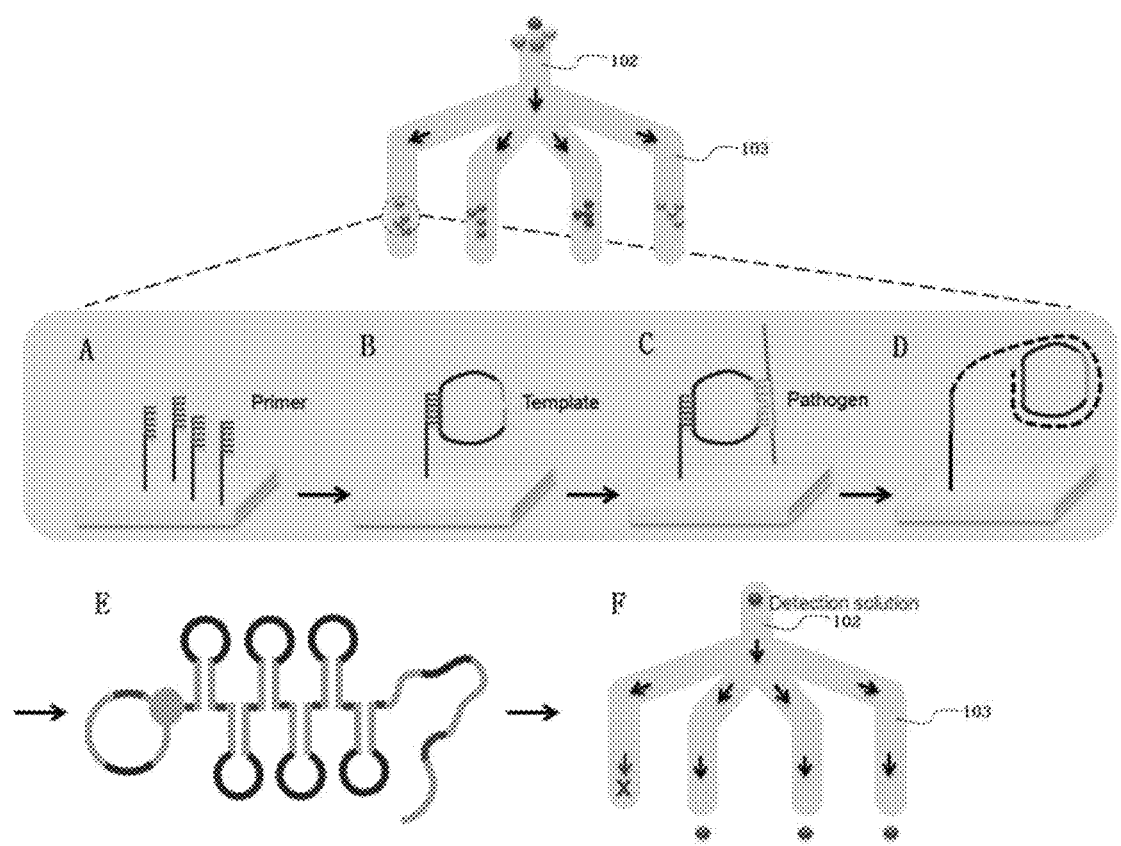
FIG. 3 illustrates a process of preparing a microfluidic device for detecting a target gene and a method of detecting a target gene using the same according to the present invention. A, B, C, D, E, and F each represent an operation of the process.

Accordingly, the primer may be immobilized on the second channel of the microfluidic device (see A of FIG. 3).

Operation 4: Operation of Combining Template Including Binding Region Complementary to Target Gene, Binding Region Complementary to Primer, and In-Template Complementary Binding Region to Form Dumbbell Shape with Primer (Primer-Template Combining Operation)

Referring to FIG. 1, a template was applied to the second channel 103 through each outlet 104, thereby combining and fixing each template with the primer immobilized on the second channel 103 having the branches. For a negative control, no template was applied to the second channel. Specifically, a template for Ebola virus (Template_E) was applied to channel 2 of the second channel having the three branches (the middle branch of the second channel of FIG. 1), a template for *Bacillus anthracis* (Template_B_A) was applied to channel 3 of the second channel (the left branch of the second channel of FIG. 1), and channel 1 was used as a negative control. Specifically, 1×PBS (Gibco by Life Technoligies) was added to 0.24 µl (=24 pmole) of 100Template_E (SEQ ID NO:11) to 6 µl and was put into channel 3. 1×PBS (Gibco by Life Technoligies) was added to 0.2 µl (=20 pmole) of 100Template_B_A (SEQ ID NO:10) to 5 µl and was put into channel 2, while 6 µl of 1×PBS (Gibco by Life Technoligies) was put into channel 1 and channel 3. After being left for two hours, the second channel was washed with DDW (Water Purification System/LABOGENE).

Accordingly, the primer immobilized on the second channel may be combined with the templates (see B of FIG. 3). Different templates for recognizing specific pathogen genes may bind to the primer immobilized on the respective branches of the second channel, thereby detecting different target genes at the same time.

<Embodiment 3> Method for Detecting Target Gene Using Microfluidic Device for Detecting Target Gene Principle of Detecting Target Gene A method for detecting a target gene using a microfluidic device for detecting a target gene is based on a principle in which a closed-form dumbbell-shaped template with a nick disappearing is ligated only in the presence of a target gene (for example, a pathogen gene) and is subsequently amplified by rolling circle amplification (RCA) to for a self-assembled precise structure of particles (see FIG. 2).

Figure 12:
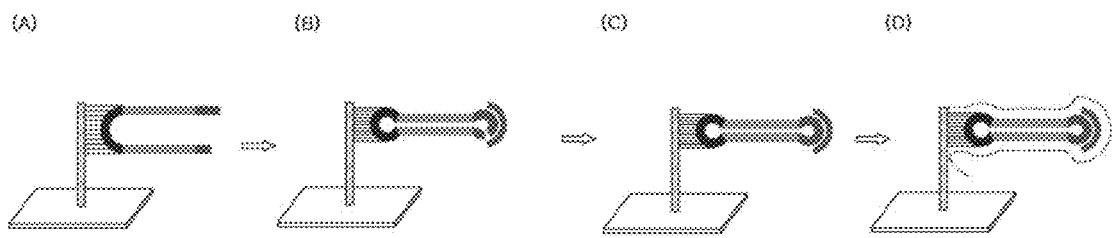
FIG. 12 is a schematic view specifically illustrating nick ligation and RCA occurring in a template binding to a primer of the microfluidic device of the present invention. A, B, C, D, and E each represent an operation of the method.

FIG. 12 is a schematic view specifically illustrating a process of FIG. 3B to FIG. 3D. That is, FIG. 12A shows that a template binds to a primer immobilized on a second channel of a microfluidic device for detecting a target gene according to the present invention. When target pathogen genes is present in a sample flowing into the second channel of the microfluidic device for detecting the target gene, the target pathogen genes bind to both a first target gene binding region and a second target gene binding region of the template (FIG. 12B and FIG. 2B). Here, as opposite ends of the first target gene binding region and the second target gene binding region become close to each other, only a small gap, that is, a nick, is present therebetween. At the same time, a first in-template complementary binding region and a second in-template complementary binding region also become close to each other to form a complementary bond. The nicks are connected to each other by a ligase as an enzyme connecting adjacent 5' and 3' ends, so that the template turns a completely closed form into a dumbbell shape (FIG. 12 and FIG. 2C).

An isothermal nucleic acid polymerase performs RCA of infinitely repetitively replicating nucleic acid using the closed-form template for detecting the target gene as a template until a dNTP is exhausted (see FIG. 12D and FIG. 2D). As a replicated portion is displaced from the template for detecting the target gene, linear nucleic acid with the repeating sequence of the template for detecting the target gene is produced. The first target gene binding region and the second target gene binding region of this linear nucleic acid are combined with the target genes, and long tangled nucleic acid mass is formed by RCA and is flocculated with a coating of the second channel into large hydrogel mass. It is observed that the produced hydrogel mass is present in the second channel and blocks an outlet connected to the second channel.

Embodiment 3-1: Method for Detecting Target Gene Using Microfluidic Device for Detecting Single Target Gene (Method for Detecting Single Target Pathogen (*Bacillus anthracis*) Gene Using Microfluidic Device for Detecting Single Target Gene)

Operation 1: Operation of Providing Microfluidic Device for Detecting Single Target Gene (Microfluidic Device for Detecting Single Pathogen (*Bacillus anthracis*) Gene) According to Embodiment 2-1

A microfluidic device for detecting a single target gene was provided (prepared). Specifically, a microfluidic device for detecting a single target gene (microfluidic device for detecting a single pathogen (*Bacillus anthracis*) gene) was provided according to Embodiment 2-1.

Operation 2: Operation of Introducing Sample Solution into First Channel (1) Preparation of Sample Solution A sample (Pathogen_BA, SEQ ID NO:12) was prepared based on the pathogen gene sequence of *Bacillus anthracis* by order from Bioneer (HPLC Purification). A sample solution was prepared using Pathogen_B_A 100 in 1×PBS.

Table 4 below illustrates the template and pathogen sequence of *Bacillus anthracis* used in Embodiment 3.

TABLE 4

| Pathogen kind | SEQ ID NO: | Template sequence (5'→3') | SEQ ID NO: | Pathogen sequence |
|---|---|---|---|---|
| *Bacillus anthracis* | 10 | 5'-phosphate TTT GAA ATG GAG AAA ATC GAA GTA CTC AGC GTA AGT TTA GAG GTA GCA TGC TAG TAT CGA CGT ACG TAC CAA CTT ACG CTG AGT ACT TCG ATT TGA GCG-3' | 12 | 5'-TTC TCC ATT TCA AAC GCT CA-phosphate-3' |

(2) Operation of Introducing Sample Solution Prepared in (1) to First Channel

60 µl of the sample solution prepared in (1) was introduced into a first channel through an inlet of the microfluidic device for detecting the single target gene. The sample solution, introduced into the first channel of the microfluidic device for detecting the single target gene, transferred by capillarity to the second channel via the first channel. After being left for two hours, the device was washed with DDW (Water Purification System, LABOGENE).

Operation 3: Ligation of Single Target Gene (Single Pathogen (*Bacillus anthracis*) Gene) Included on Sample Solution and Template The sample solution introduced into the first channel flowed into the second channel by capillarity.

Next, the second channel of the microfluidic device for detecting the single target gene was filled with 30 μl of 2× T7 ligase, 5 μl of T7 ligase 5, 0.2 μl of 100 mM DTT, and 24.8 μl of DDW (Water Purification System/LABOGENE). To prevent the evaporation of moisture in the device, the mixtures were allowed to react with the sample solution in a plastic container sealed with a parafilm. The plastic container was filled with tissue dampened with water and 25° C. water. Next, the reactants were subjected to reaction with no shaking at 25° C. for three hours in a shaking incubator (VS-8480 (VISION SCIENNTIFIC CO)).

Operation 4: Amplification (Rolling Circle Amplification) of Ligated Gene Product Next, the second channel of the microfluidic device for detecting the single target gene was filled with 2 μl of 25 mM dNTP, 6 μl of 10× T7 ligase reaction buffer (Biolabs), 50 μl of phi 29 polymerase (10 unit/μl), 1 μl of pyrophosphatase, and 1 μl of 100 mM DTT. Reaction was carried out in a plastic container sealed with a parafilm in order to prevent the evaporation of moisture in the second channel of the microfluidic device for detecting the single target gene. The plastic container was filled with tissue dampened with water and 30° C. water. Next, the reactants were subjected to reaction with no shaking at 30° C. for three hours in a shaking incubator (VS-8480 (VISION SCIENNTIFIC CO)).

Operation 5: Detection of Amplified Target Gene Product (Identification of Detected Target Gene)

50 μl of a 1:1000 GelRed (GelRed™, Biotium) dilution (diluted with DDW (Water Purification System, LABOGENE)) was added as a detection composition through the inlet. A 1:200 GelRed (GelRed™, Biotium) dilution was allowed to flow to the second channel via the first channel. Although GelRed (GelRed™, Biotium) diluted at 1:10000 is generally used, the dilution rate of GelRed is adjusted to see the color with the naked eye and is not limited thereto.

Referring to a of FIG. 9, a red mark in channel 2 is a DNA membrane, and it is possible to detect the amplified target gene product using a dye reagent, such as GelRed, as a detection composition. Further, referring to b of FIG. 9, it is easily recognized using an imager (Gel Doc™ EZ, Bio-Rad) that flow in channel 2 of the microfluidic device for detecting the single target gene is blocked. Accordingly, it is identified that the microfluidic device for detecting the single target gene according to the present invention enables the detection of a single target gene, for example, a single pathogen (*Bacillus anthracis*) gene, with the naked eye at a warm temperature, for example, a temperature of 30° C., without using a thermo cycler and without specially changing temperature.

Embodiment 3-2: Method for Detecting Target Gene Using Microfluidic Device for Detecting Two or More Target Genes (Method for Detecting Single Target Pathogen (*Bacillus Anthracis* and Ebola Virus) Gene Using Microfluidic Device for Detecting Two or More Target Genes)

Operation 1: Operation of Providing Microfluidic Device for Detecting Two or More Target Genes (Microfluidic Device for Detecting Two or More Pathogen (*Bacillus Anthracis* and Ebola Virus) Genes) According to Embodiment 2-2

A microfluidic device for detecting two or more target genes was provided (prepared). Specifically, a microfluidic device for detecting two or more target genes (microfluidic device for detecting two or more pathogen (*Bacillus anthracis* and Ebola virus) genes) was provided according to Embodiment 2-2.

Operation 2: Operation of Introducing Sample Solution into First Channel (1) Preparation of Sample Solution A sample (Pathogen_BA, SEQ ID NO:12) was prepared based on the pathogen gene sequence of *Bacillus anthracis* by order from Bioneer (HPLC Purification). A sample solution was prepared using Pathogen_B_A 100 in 1×PBS.

(2) Preparation of Sample

Samples (Pathogen_BA, SEQ ID NO:12 and Pathogen_E, SEQ ID NO:13) were prepared based on the pathogen gene sequences of *Bacillus anthracis* and Ebola virus by order from Bioneer (HPLC Purification). A sample solution was prepared using Pathogen_B_A 100 in 1×PBS. Further, a sample solution was prepared using Pathogen_E 100 in 1×PBS.

Table 5 below illustrates the templates and pathogen sequences of *Bacillus anthracis* and Ebola virus used in Embodiment 2.

| Pathogen kind | SEQ ID NO: | Template sequence (5'→3') | SEQ ID NO: | Pathogen sequence |
|---|---|---|---|---|
| *Bacillus anthracis* | 10 | 5'-phosphate-TTT GAA ATG GAG AAA ATC GAA GTA CTC AGC GTA AGT TTA GAG GTA GCA TGC TAG TAT CGA CGT ACG TAC CAA CTT ACG CTG AGT ACT TCG ATT TGA GCG-3' | 12 | 5'-TTC TCC ATT TCA AAC GCT CA-phosphate-3' |
| *Ebola virus* | 11 | 5'-phosphate-GA CGC ACG CG A ATC GAA GTA CTC AGC GTA AGT TTA GAG GTA GCA TGC TAG TAT CGA CGT ACG TAC CAA CTT ACG CTG A GT ACT TCG ATT AAC GAG AAA TCG CAC-3' | 13 | 5'-CGC GTG CGT CGT GCG ATT TCT CGT T-phosphate-3' |

(2) Operation of Introducing Sample Solution Prepared in (1) to First Channel

60 µl of the sample solution prepared in (1) was introduced into a first channel through an inlet of the microfluidic device for detecting the single target gene. The sample solution, introduced into the first channel of the microfluidic device for detecting the single target gene, transferred to the second channel via the first channel. 5 µl of total 20 µl Template_E and 5 µl of total 20 µl Template_B_A were put into channel 2 and channel 3 of the second channel. After being left for two hours, the device was washed with DDW (Water Purification System, LABOGENE).

Operation 3: Ligation of Two or More Target Genes (Two or More Pathogen (*Bacillus Anthracis* and Ebola Virus) Genes)) Included in Sample Solution and Template The second channel of the microfluidic device for detecting the single target gene was filled with 30 µl of 2× T7 ligase, 5 µl of T7 ligase 5, 0.2 µl of 100 mM DTT, and 24.8 µl of DDW (Water Purification System/LABOGENE). To prevent the evaporation of moisture in the device, reaction was carried out in a plastic container sealed with a parafilm. The plastic container was filled with tissue dampened with water and 25° C. water. Next, the reactants were subjected to reaction with no shaking at 25° C. for three hours in a shaking incubator (VS-8480 (VISION SCIENNTIFIC CO)).

Accordingly, the target gene (pathogen gene) present in the sample complementarily bound to the specific template to form a ring-shaped template (see C of FIG. 3).

Operation 4: Amplification (Rolling Circle Amplification) of Ligated Gene Product <Method 1>

Next, the second channel of the microfluidic device for detecting the two or more target genes was filled with 2 µl of 25 mM dNTP, 6 µl of 10× T7 ligase reaction buffer (Biolabs), 50 µl of phi 29 polymerase (10 unit/µl), 1 µl of pyrophosphatase, and 1 µl of 100 mM DTT. Reaction was carried out in a plastic container sealed with a parafilm in order to prevent the evaporation of moisture in the second channel of the microfluidic device for detecting the two or more target genes. The plastic container was filled with tissue dampened with water and 30° C. water. Next, the reactants were subjected to reaction with no shaking at 30° C. for three hours in a shaking incubator (VS-8480 (VISION SCIENNTIFIC CO)).

<Method 2>

Next, the second channel of the microfluidic device for detecting the two or more target genes was filled with 2 µl of 25 mM dNTP, 1 µl of 0.4 mM Biotin-14-dCTP, 2 µl of 10× T7 ligase reaction buffer (Biolabs), 5 µl of phi 29 polymerase (500 unit/µl), 1 µl of pyrophosphatase, 0.8 µl of 100 mM DTT, and 6.2 µl of DDW. Reaction was carried out in a plastic container sealed with a parafilm in order to prevent the evaporation of moisture in the second channel of the microfluidic device for detecting the two or more target genes. The plastic container was filled with tissue dampened with water and 30° C. water. Next, the reactants were subjected to reaction at 30° C. for three hours in a shaking incubator (VS-8480 (VISION SCIENNTIFIC CO)).

The target gene (nucleic acid) may be amplified by RCA according to Method 1 or Method 2 (see D of FIG. 3).

Operation 5: Detection of Amplified Target Gene Product (Identification of Detected Target Gene)

A tangled single-strand rolling-circle-amplified gene product (see E of FIG. 3) may selectively block each branch of the second channel of the microfluidic device, and thus it is possible to detect the gene. A detection composition may be added to the second channel of the microfluidic device, thereby facilitating detection (see F of FIG. 3).

<Detection Method Related to Method 1 of Operation 4>

50 µl of a 1:1000 GelRed (GelRed™, Biotium) dilution (diluted with DDW (Water Purification System, LABOGENE)) was added as a detection composition through the inlet. A 1:80 GelRed (GelRed™, Biotium) dilution was allowed to flow to the second channel via the first channel.

Figure 10A:
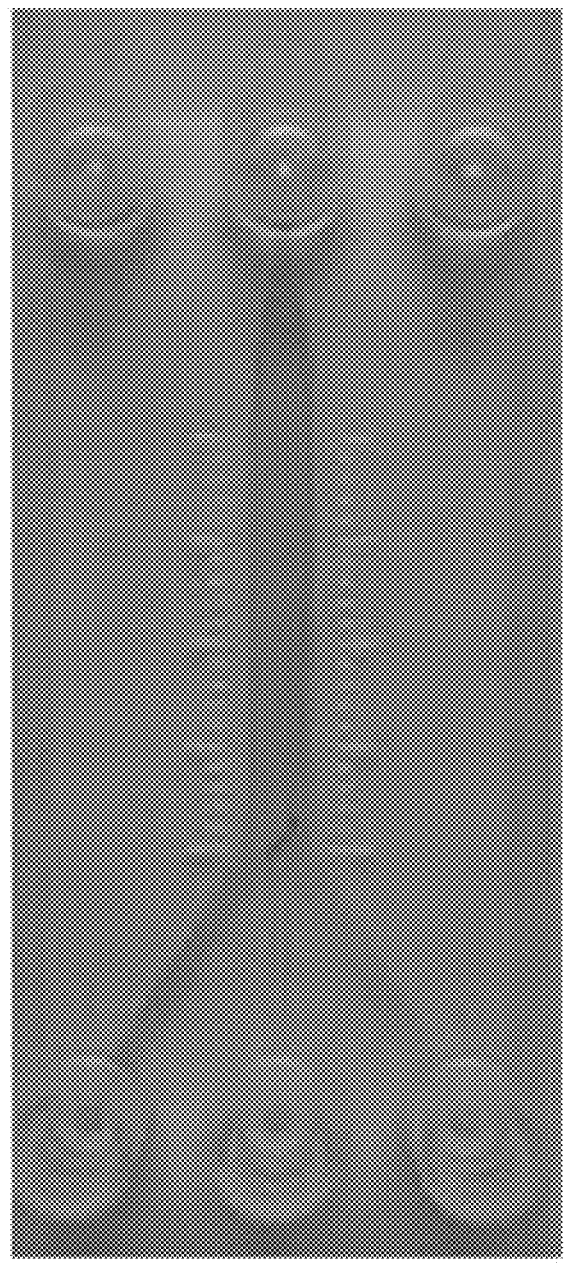
FIG. 10a is a picture showing a result of simultaneously detecting *Bacillus anthracis* and Ebola virus using the microfluidic device of the present invention.
Figure 10B:
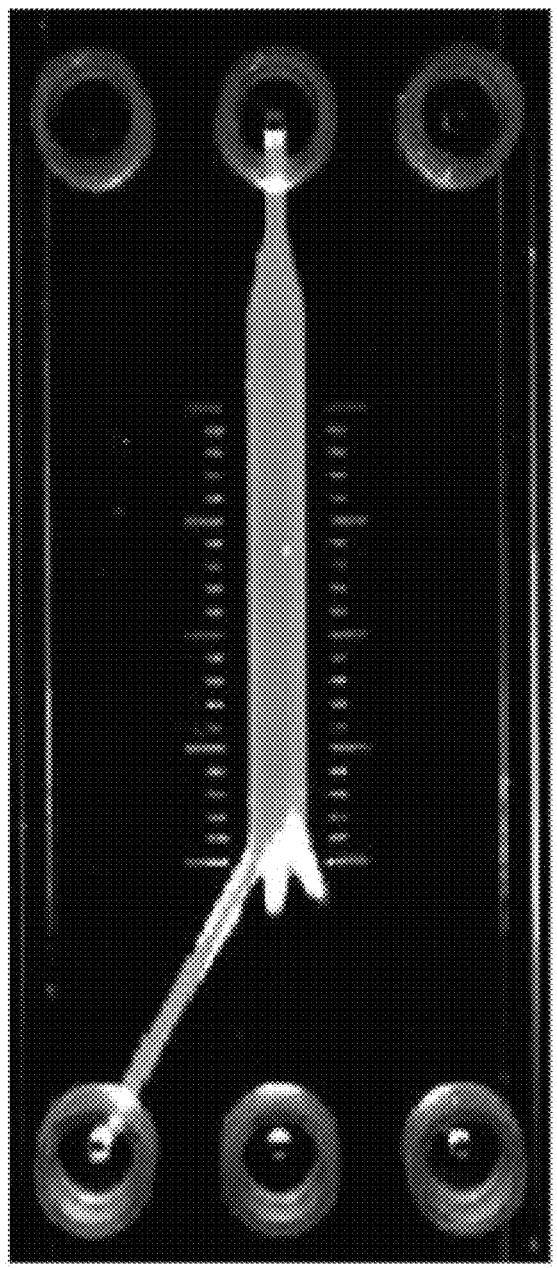
FIG. 10b is a picture showing a result of identifying *Bacillus anthracis* and Ebola virus using an imager (Gel Doc™ EZ, Bio-Rad).

Referring to b of FIG. 10, it is easily recognized using an imager (Gel Doc™ EZ, Bio-Rad) that flow in channel 2 and channel 3 of the microfluidic device for detecting the two or more target genes is blocked. Accordingly, it is identified that the microfluidic device for detecting the two or more target genes according to the present invention enables the simultaneous detection of two or more target genes, for example, two or more pathogen (*Bacillus anthracis* and Ebola virus) genes, with the naked eye at a warm temperature, for example, a temperature of 30° C., without using a thermo cycler and without specially changing temperature.

<Detection Method Related to Method 2 of Operation 4>

Streptavidin beads were used as a detection composition. Specifically, 50 µl of a 1:20 Streptavidin Fluorosbrite YG Microspheres 2.0 Micro dilution (diluted with DDW (Water Purification System, LABOGENE)) was added through the inlet.

Figure 11:
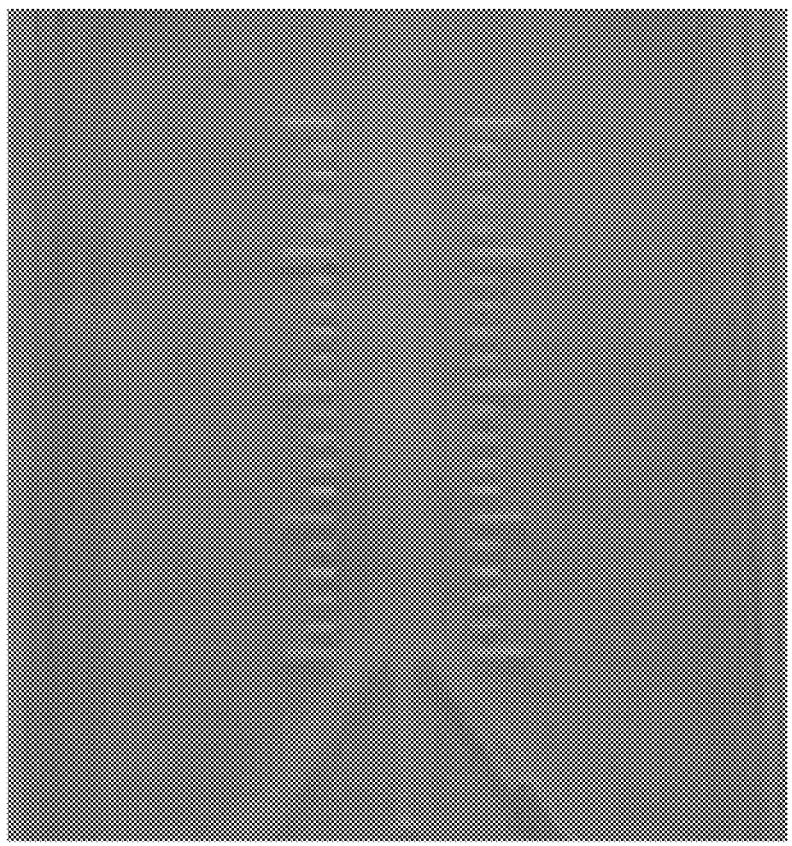
FIG. 11 shows a result of detecting *Bacillus anthracis* and Ebola virus using Streptavidin and the microfluidic device of the present invention.

Referring to FIG. 11, it is easily recognized that flow in channel 2 and channel 3 of the microfluidic device for detecting the two or more target genes is blocked by an air layer due to an RCA product or is blocked by an RCA product further tangled by the reaction of biotin of the RCA product and streptavidin. Accordingly, it is identified that the microfluidic device for detecting the two or more target genes according to the present invention enables the simultaneous detection of two or more target genes, for example, two or more pathogen (*Bacillus anthracis* and Ebola virus) genes, with the naked eye at a warm temperature, for example, a temperature of 30° C., without using a thermo cycler and without specially changing temperature.

<Experimental Embodiment 1> Identification of Electrophoresis Result of Each Operation An experiment was conducted to identify binding and ligation of Template_BA manufactured in Preparative Embodiment 1 and the pathogen using an electrophoresis result. In Experimental Embodiment 1, the experiment was simply performed in a tube to identify reaction of the template of Preparative Embodiment 1 and the pathogen. Further, a thermo cycler was used for tests in different reaction conditions. In addition, an experiment was conducted to identify binding and ligation of Template_E manufactured in Preparative Embodiment 1 and the pathogen using an electrophoresis result. In the tube experiment, since the template was not immobilized to the primer, phosphate was not attached to the 3' end of each pathogen, that is, the 3' end of the pathogen gene.

(1) Identification of Annealing Operation

A template for 100 *Bacillus anthracis* (Template_BA, SEQ ID NO:10) was diluted with DEPC (Sigma-Aldrich) as a solvent into 1Template_BA. 3.2 µl of DDW (Water Purification System, LABOGENE), 1 µl of 10×PBS with pH 7.4 (Gibco by Life Technologies), and 5 µl of 40 mM $MgCl_2$ (Sigma-Aldrich) were sequentially put into a tube, to which 0.8 µl (that is, 0.8 pmole) of 1Template_BA was added. Subsequently, temperature was decreased for one hour from 95° C. to 4° C. using a thermo cycler (Bio-Rad T100™).

Next, 2 μl of a loading dye (Gel Loading Dye Blue 6×, Biolabs) was added, followed by electrophoresis in a 15% PAGE in 1× Tris-borate-EDTA (TBE) buffer (150 V, 45 minutes) and dying with GelRed (GelRed™, Biotium), thereby identifying an electrophoresis result using Gel Doc™ EZ (Bio-Rad).

An experiment for identifying an annealing operation was conducted in the same manner except for using Template_E (SEQ ID NO:11) instead of Template_BA.

(2) Identification of Hybridization Operation

An experiment was conducted as follows to identify hybridization of *Bacillus anthracis* (Pathogen_BA Not Phosp, SEQ ID NO:14) in the sample and the template. First, 2 μl of DDW (Water Purification System, LABOGENE), 1 μl of 10×PBS with pH 7.4 (Gibco by Life Technologies), and 5 μl of 40 mM $MgCl_2$ (Sigma-Aldrich) were sequentially put into a tube, to which 1 μl of 10Pathogen_BA_Not Phosp and 1 μl of 10Template_B_A were added. Subsequently, temperature was decreased for one hour from 95° C. to 4° C. using a thermo cycler (Bio-Rad T100™).

Next, 1 μl (that is 0.8 pmol) of the template was diluted with 9 μl of 1×PBS to have a total volume of 10 μl, after which 2 μl of a loading dye (Gel Loading Dye Blue 6×, Biolabs) was added, followed by electrophoresis in a 15% PAGE in 1× Tris-borate-EDTA (TBE) buffer (150 V, 45 minutes) and dying with GelRed (GelRed™, Biotium), thereby identifying an electrophoresis result using Gel Doc™ EZ (Bio-Rad).

A hybridization operation was identified in the same manner except for using Template_E (SEQ ID NO:11), instead of Template_BA (SEQ ID NO:1), and using Template_E_Not Phosp (SEQ ID NO:15), instead of Pathogen_BA_Not Phosp (SEQ ID NO:14).

(3) Identification of Ligation Operation 2.4 μl of DDW (Water Purification System, LABOGENE), 10 μl of 2× T7 ligase reaction buffer (Biolabs), 1.6 μl of 100Pathogen_BA_Not Phosp (SEQ ID NO:14), and 0.8 μl of 100Template_BA (SEQ ID NO:10) were sequentially put into a tube, and temperature was decreased for five minutes from 95° C. to 4° C. using a thermo cycler (Bio-Rad T100™). Next, 0.2 μl of 100 mM DTT (Epicenter RepliPHI Phi29 reagent set (0.1 μg/μl)) and 5 μl of T7 ligase (Biolabs) were added. Then, temperature was maintained at 25° C. for 13 hours, at 65° C. for 20 minutes, and at 10° C. using the thermo cycler (Bio-Rad T100™). As a result, 20 μl of 4 ligation product was obtained. 2 μl of a loading dye (Gel Loading Dye Blue 6×, Biolabs) was added to 0.8 pmole of the ligation product, followed by electrophoresis in a 15% PAGE in 1× Tris-borate-EDTA (TBE) buffer (150 V, 45 minutes) and dying with GelRed (GelRed™, Biotium), thereby identifying an electrophoresis result using Gel Doc™ EZ (Bio-Rad).

A ligation operation was identified in the same manner except for using Template_E (SEQ ID NO:11), instead of Template_BA (SEQ ID NO:1), and using Template_E_Not Phosp (SEQ ID NO:15), instead of Pathogen_BA_Not Phosp (SEQ ID NO:14).

(4) Rolling Circle Amplification 7.2 μl of DDW (Water Purification System, LABOGENE), 2 μl of 10× T7 ligase reaction buffer (Biolabs), and Epicenter RepliPHI Phi29 reagent set (0.1 μg/μl) were sequentially put into a tube, to which 2 μl (8 pmole) of 4 ligation product obtained in the ligation operation was added. Subsequently, 2 μl of 25 mM dNTP (Epicenter RepliPHI Phi29 reagent set (0.1 μg/μl)), 0.8 μl of 100 mM DTT (Epicenter RepliPHI Phi29 reagent set (0.1 μg/μl)), 1 μl of Pyrophosphatase (100 U/ml, Biolabs), and 5 μl of Phi 29 polymerase (Epicenter RepliPHI Phi29 reagent set (0.1 μg/μl)) were sequentially added. Then, temperature was maintained at 30° C. for 15 hours, at 65° C. for 10 minutes, and at 4° C. using the thermo cycler (Bio-Rad T100™).

(5) Identification of Electrophoresis Result

Figure 4:
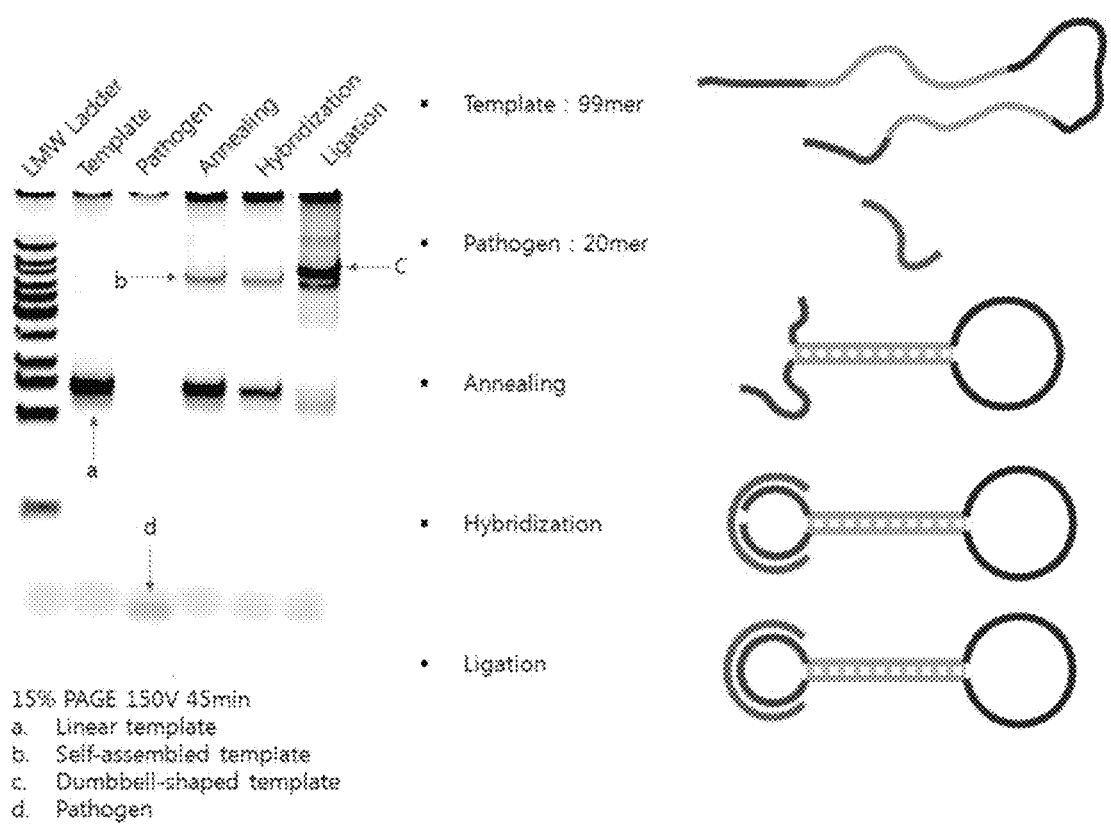
FIG. 4 illustrates an electrophoresis result showing a ligation of a dumbbell template (Template_B_A) in a tube by for detecting *Bacillus anthracis*.

Based on a DNA Ladder (Quick-Load LMW Ladder, Biolabs), the template (Template_BA, SEQ ID NO:10), the pathogen (Pathogen_BA_Not Phosp, SEQ ID NO:14), and 0.8 pmole of each of the products obtained in Operations (1) to (3) were loaded and were subjected to electrophoresis, results of which are illustrated in FIG. 4.

Referring to FIG. 4, the template generally has a linear form, that is, is a linear template (see a of FIG. 4). In the template, in-template complementary binding regions to form a dumbbell shape complementarily bound to each other to be annealed under self-assembly conditions, thereby forming a self-assembled form, that is, a self-assembled template (see b of FIG. 4). When a target gene, for example, a pathogen gene, bound to a binding region complementary to a target gene in the self-assembled template, the template was formed into a closed-form dumbbell-shaped template with a nick disappearing and was ligated (see c of FIG. 4). Subsequently, the ligated product was subjected to RCA.

<Experimental Embodiment 2> Identification of SEM Image of RCA Product (1) Identification of *Bacillus anthracis*

20 μl of the RCA product, obtained using Template_B_A manufactured in Preparative Embodiment 1 according to method (4) of Experimental Embodiment 1, was mixed with 2 μl of 2M $MgCl_2$ and was slowly cooled (from 95° C. to 4° C. for one hour), so that a white DNA ball of about 1 mm was formed.

Figure 5:
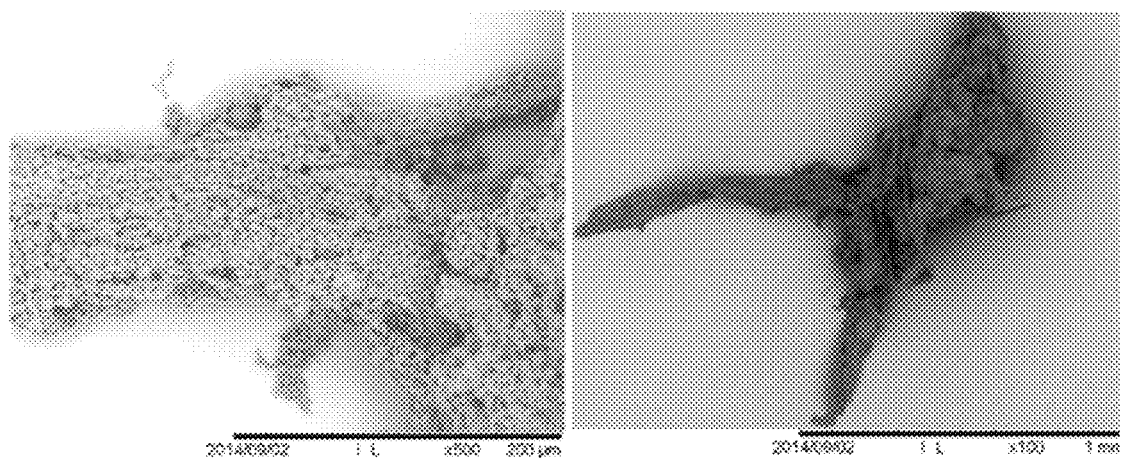
FIG. 5 is an SEM image showing that an RCA product is identified in a tube using a template for *Bacillus anthracis* (Template_B_A) in (1) of Experimental Embodiment 2.

The DNA ball was dried for 24 hours on glassware (MARIENFELD), was bound to mica (Pelco Mica sheets, Ted Pella Corp.), and was photographed with an SEM (Tm3030 tabletop microscope, Hitachi High-Tech). As shown in FIG. 5, delicate single-strand DNA mass was formed.

(2) Identification of Ebola Virus

Figure 6:
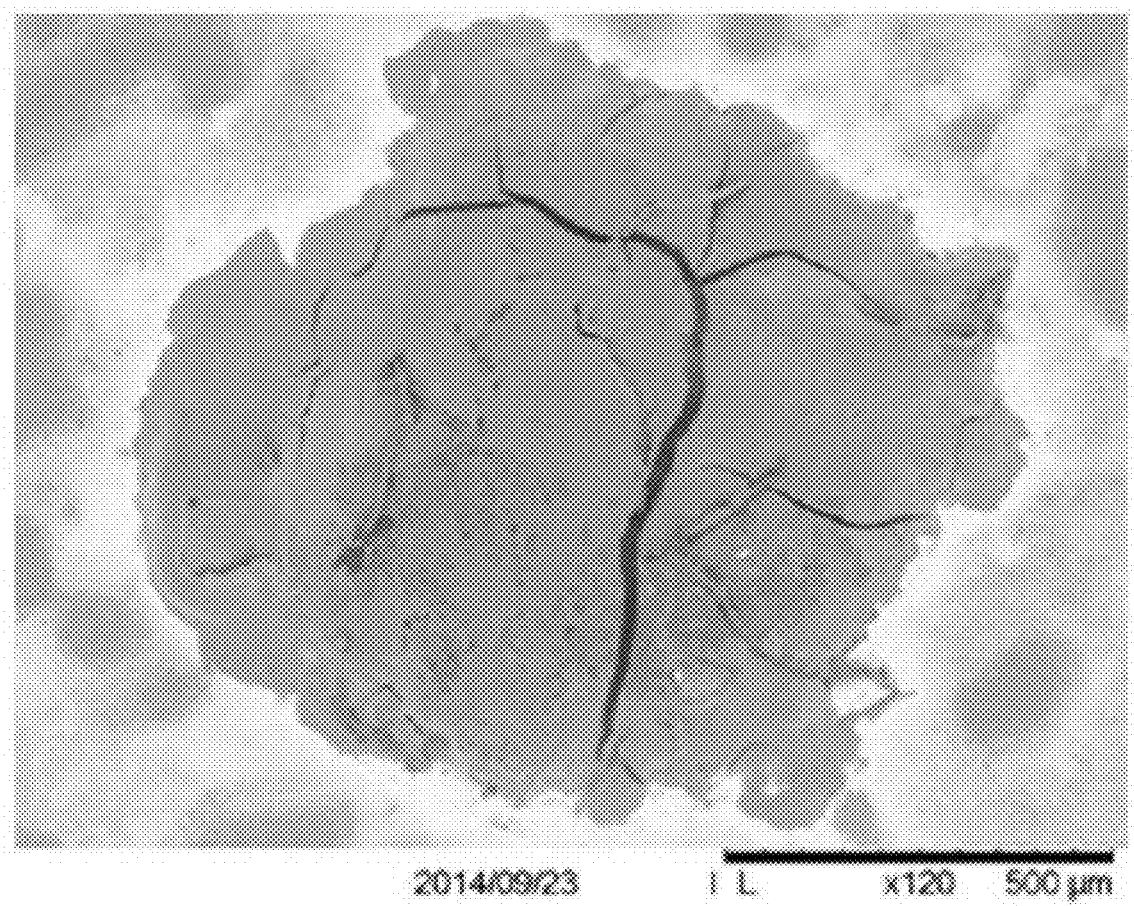
FIG. 6 is an SEM image showing that an RCA product is identified in a tube using a template for Ebola virus (Template_E) in (2) of Experimental Embodiment 2.

20 μl of the RCA product, obtained using Template_E manufactured in Preparative Embodiment 1 according to method (3) of Experimental Embodiment 1, was mixed with 5M $NH_4OAc$ 40 (SIGMA-Aldrich), and 100% EtOH 500 was added to the mixture, followed by freezing for 20 minutes. The resulting product was subjected to centrifugation (10,000 rpm, 20 minutes, 4° C.), and 40 μl of the supernatant was sonicated (BRANSON 5510) for 30 minutes. The product was dried for 24 hours on glass, was bound to mica (Pelco Mica sheets, Ted Pella Corp.), and was photographed with an SEM (Tm3030 tabletop microscope, Hitachi High-Tech). As shown in FIG. 6, an amplified gene product of tangled-strand mass was formed.

<Experimental Embodiment 3> Identification of Hydrogel Formation of RCA Gene Product An experiment was conducted to identify whether the amplified gene product obtained by RCA in Experimental Embodiment 1 formed hydrogel. *Bacillus anthracis* (Pathogen_BA Not Phosp, SEQ ID NO:14) and Ebola virus (Pathogen_E Not Phosp, Sequence No. 15) were used as pathogens.

In Experimental Embodiment 3, the experiment was simply performed in a tube to identify reaction of the template of Preparative Embodiment 1 and the pathogens. Further, a thermo cycler was used for tests in different reaction conditions.

For viscosity measurement due to hydrogel formation, viscosity and rotational viscosity measurement was performed using a tube and a pipette tip.

(1) Viscosity Measurement using Tube and Pipette Tip

The flowability of a reactant liquid (solution containing the RCA product obtained in (4) of Experimental Embodiment 1) was measured while tilting the tube 90 degrees based on the major axis of the tube. No flowability identified for 60 seconds indicated that a target gene, for example, a pathogen gene (Template_BA or Template_E), was detected.

Figure 7A:
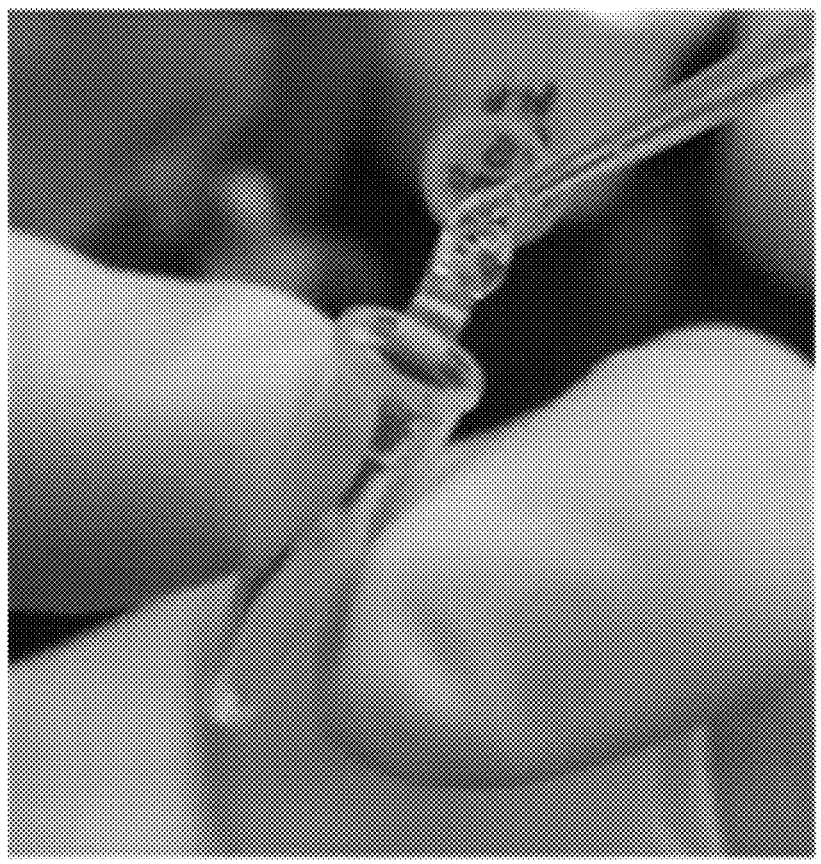
FIG. 7a shows a result of the formation of hydrogel in a tube by a template for Ebola virus (Template_E)
Figure 7B:
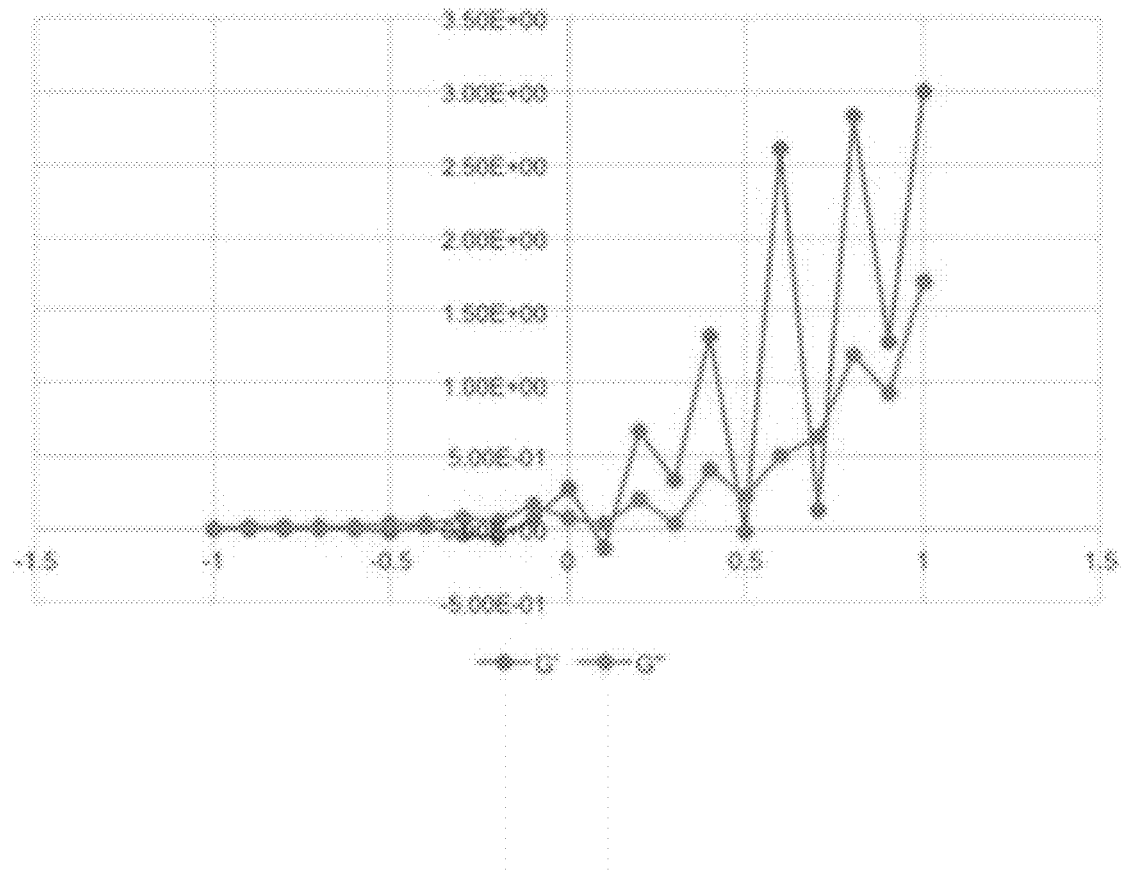
FIG. 7b is a graph of viscosity measured with a rotational viscometer.

Further, when a reactant liquid (solution containing the RCA product obtained in (4) of Experimental Embodiment 1) was drawn (sucked) using a pipette tip, the reactant liquid (solution containing the RCA product obtained in (4) of Experimental Embodiment 1) was sucked up along the surface of the pipette tip due to a viscosity change. When the liquid has a similar level of viscosity to that of water, no liquid was sucked up along the tip. However, when the liquid increased in viscosity, the material was more sucked up along the tip and returned (see a of FIG. 7).

In RCA using Template_BA or Template_E, manufactured in Preparative Embodiment 1, the product had viscosity to hardly exhibit flowability for 60 seconds, making it possible to detect a target gene, for example, a pathogen gene (Template_BA or Template_E). Further, it was identified that hydrogel with higher viscosity was formed using Template_E having a larger length complementary to a pathogen than using Template_BA.

(2) Measurement with Rotational Viscometer

The viscosity change of an amplified gene product obtained by RCA disclosed in Experimental Embodiment 1 using Template_E, manufactured in Preparative Embodiment 1, was measured using a rotational viscometer. An increase in the viscosity change of a reactant liquid (solution containing the RCA product obtained in (4) of Experimental Embodiment 1) and a ratio between storage modulus (G') and loss modulus (G") were measured, results of which are illustrated in b of FIG. 7 (x axis: frequency (Hz), y axis: Pascal (Pa)). An increase in viscosity change by hydrogel formation indicated the possibility of detecting a target gene, for example, Ebola virus, <Experimental Embodiment 4> Identification of Effect of Coating of Second Channel of Microfluidic Device for Detecting Target Gene After performing a method for detecting a target gene using the microfluidic device for detecting the target gene according to the method of Embodiment 3-1, the second channel was observed with an atom-probe microscope (AFM, NX-10, Park System). After performing the method for detecting the target gene (method of Embodiment 3-1) using a microfluidic device for detecting a single target gene manufactured by the method for manufacturing the microfluidic device for detecting the single target gene of Embodiment 2-1 except for not performing the process of Operation 2 (without the process of coating the second channel with 5-hydroxydopamine HCl), the second channel was observed with an atom-probe microscope (AFM, NX-10, Park System).

Figure 8A:
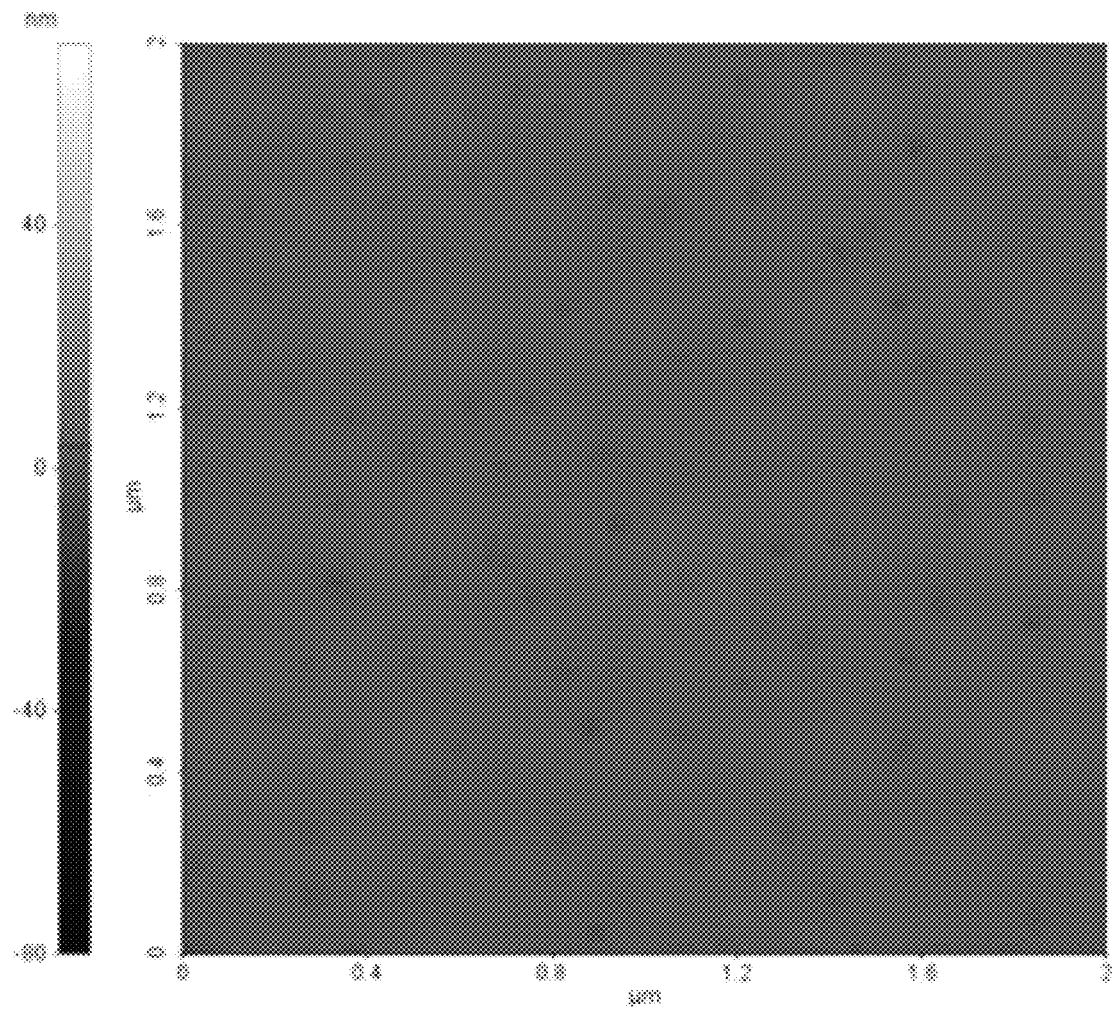
FIG. 8a is an AFM image of an RCA result in the case of immobilizing a primer on an uncoated second channel of a microfluidic device.
Figure 8B:
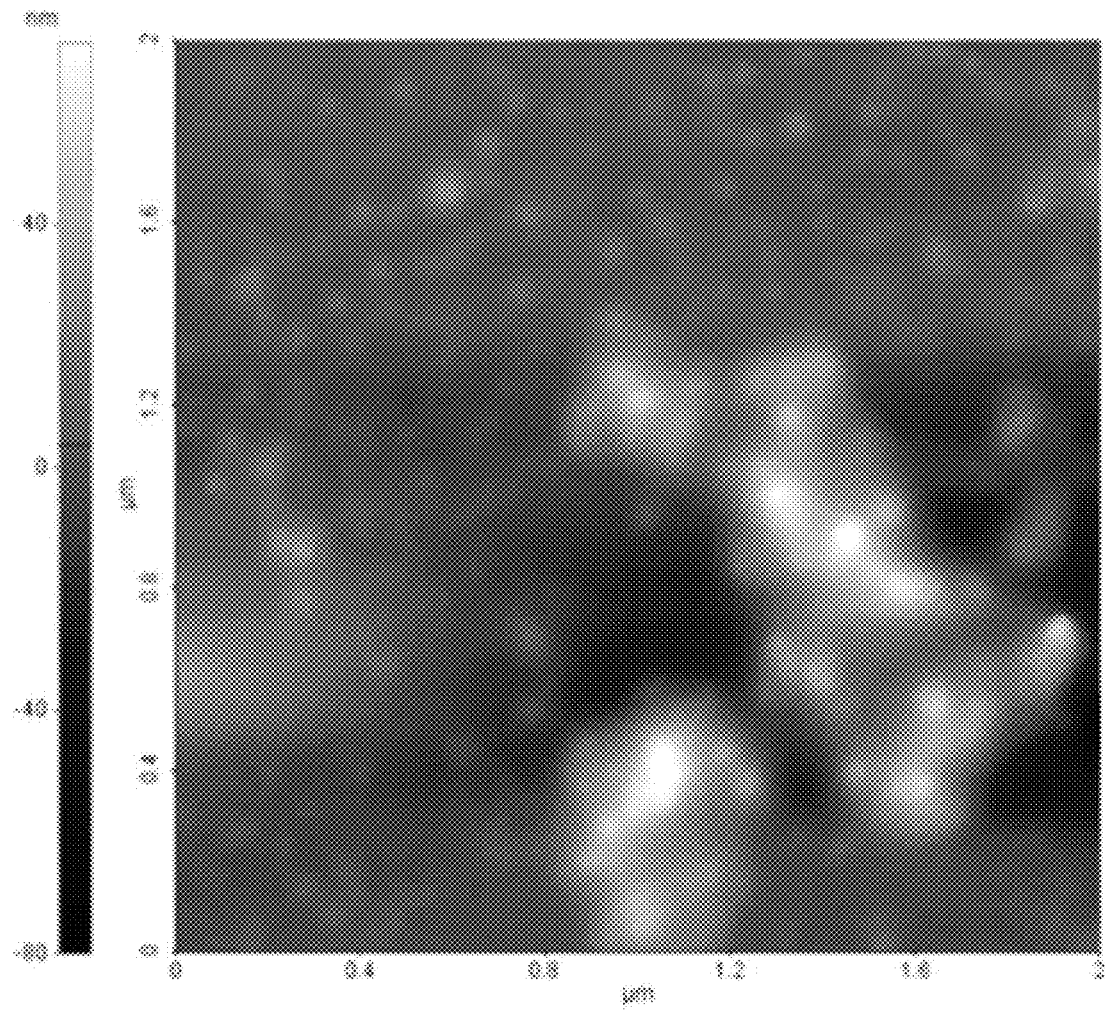
FIG. 8b is an AFM image of an RCA result in the case of immobilizing a primer on a second channel coated with 5-hydroxydopamine HCl.
Figure 9A:
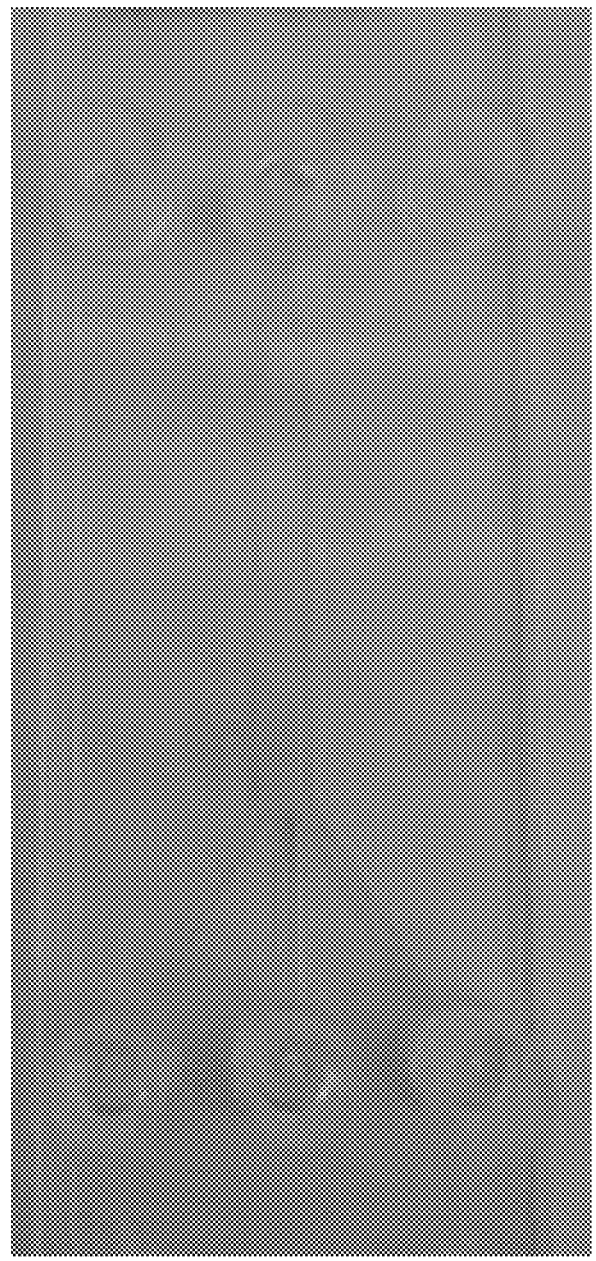
FIG. 9a is a picture showing a result of detecting *Bacillus anthracis* using the microfluidic device of the present invention.
Figure 9B:
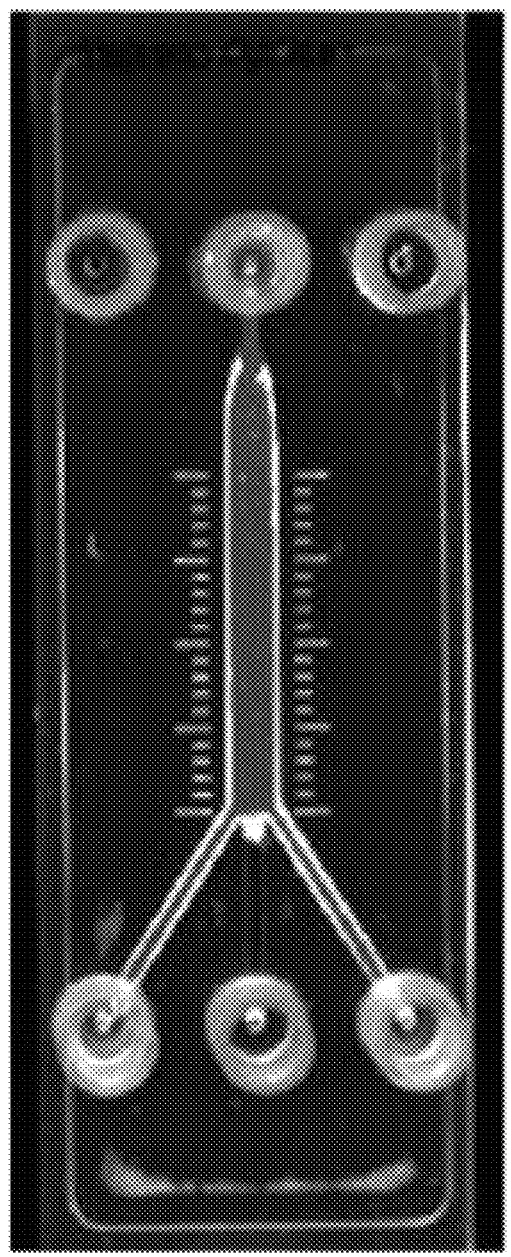
FIG. 9b is a picture showing a result of identifying *Bacillus anthracis* using an imager (Gel Doc™ EZ, Bio-Rad).

As a result, when a primer was immobilized without the process of coating using 5-hydroxydopamine HCl (pretreatment process using 5-hydroxydopamine HCl) (a of FIG. 8), the primer was hardly attached to the surface of the board, and thus no amplification occurred on the second channel of the microfluidic device for detecting the target gene. On the contrary, when a target gene (nucleic acid) was amplified after performing the process of coating using 5-hydroxydopamine HCl (pretreatment process using 5-hydroxydopamine HCl) and immobilizing a primer (b of FIG. 8), the nucleic acid was actively amplified on the second channel of the microfluidic device for detecting the target gene. Accordingly, it was shown that 5-hydroxydopamine HCl effectively immobilized a DNA primer on the second channel of the microfluidic device for detecting the target gene.

Thus, when coating the second channel of the microfluidic device for detecting the target gene with 5-hydroxydopamine HCl, 5-hydroxydopamine HCl reacted with the primer containing a thiol group, so that the primer was effectively immobilized on the second channel of the microfluidic device for detecting the target gene, thus increasing the amplification of nucleic acid by a subsequent process.

<Experimental Embodiment 5> Detection of MERS Virus Using Microfluidic Device for Detecting Target Gene (1) Manufacture of Microfluidic Device for Detecting Target MERS Gene As described above in Operation 1 and Operation 2 of Embodiment 2, a device including an inlet, a first channel, three second channels, and outlets formed at the end of the second channels, which are formed on a board, was prepared as in FIG. 1. Although 5-hydroxydopamine HCl was introduced into the second channels to coat the second channels in Embodiment 2, the second channels of plastic material were coated with a vinyl group by vapor deposition in the present experimental embodiment. Coating by the same method as in Embodiment 2 is also possible. Then, the device was washed with DDW.

Next, as in Operation 3 of Embodiment 2, a mixture solution of Primer-5SS-polyA9 (BIONEER, SEQ ID NO:9) as a primer and DTT was introduced through the inlet. A thiol group present in the primer was exposed by DTT, and the exposed thiol group bound to a vinyl coating (or 5-hydroxydopamine HCl coating) on the second channel. Next, washing with DDW was performed.

Solutions of 0.2 μl (=20 pmole) of different template 100 diluted with 1×PBS (Gibco by Life Technologies) were added to the primer immobilized on the three second channels, so that each template bound to the primer.

Specifically, Template_BA (template for *Bacillus anthracis*, SEQ ID NO:10) obtained in (1) of Preparative Embodiment 1 was bound to the left second channel from a top view. This second channel is a negative control (NC). Even though the MERS virus is present in a sample introduced into the microfluidic device, the MERS virus does not react with the template, thus not causing RCA.

A template for the MERS virus (MERS-CoV) was bound to the middle second channel. The middle second channel is a sample. Only when the MERS gene is present in a sample introduced into the microfluidic device, RCA occurs. The template for the MERS virus has the following sequence.

```
Template MERS
5'/5Phos/AGG GCA CAT CTC CGA ATC GAA GTA CTC AGC

GTA AGT TTA GAG GTA GCA TGC TAG TAT CGA CGT ACG

TAC CAA CTT ACG CTG AGT ACT TCG ATT ATA CCC-3'
```

In the template MERS sequence, a region complementary to target MERS-CoV genes are indicated in bold type in a white background, in-template complementary regions are indicated in underlined italic type, and a binding region complementary to the primer is indicated in underlined italic type.

The template for the MERS virus was bound to the primer immobilized on the second channel in the right second channel from the top view, and a target MERS gene to bind to the template was added to always cause RCA. The right second channel is a positive control (PC).

(2) Detection of Target MERS Gene

Next, a sample including a MERS virus gene to bind to the template for the MERS virus was introduced through the inlet of the microfluidic device manufactured in (1). Subsequently, ligation was allowed to occur at 25° C. overnight, and RCA was allowed to occur at 25° C. for four hours. Ligation time and RCA time may be adjusted depending on conditions. For example, when a result is identified using fluorescence, ligation time and RCA time may be adjusted to be even shorter. For example, observation may be performed after two-hour ligation and two-hour RCA.

Figure 13:
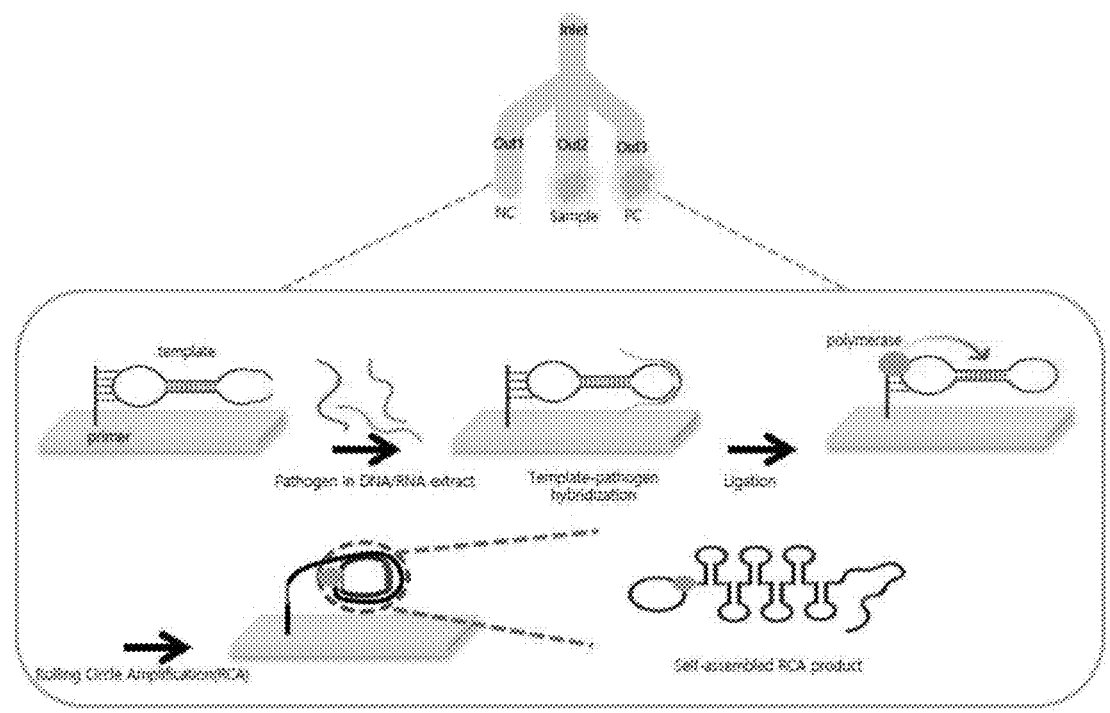
FIG. 13 is a schematic view illustrating a method for detecting a target gene using the microfluidic device of the present invention, which is manufactured to have three second channels (negative control, sample, and positive control) as in Experimental Embodiment 5.

FIG. 13 is a schematic view illustrating a process occurring in the microfluidic device having the three second channels, which are the NC, the sample, and the PC, as in Experimental Embodiment 5.

Figure 14:
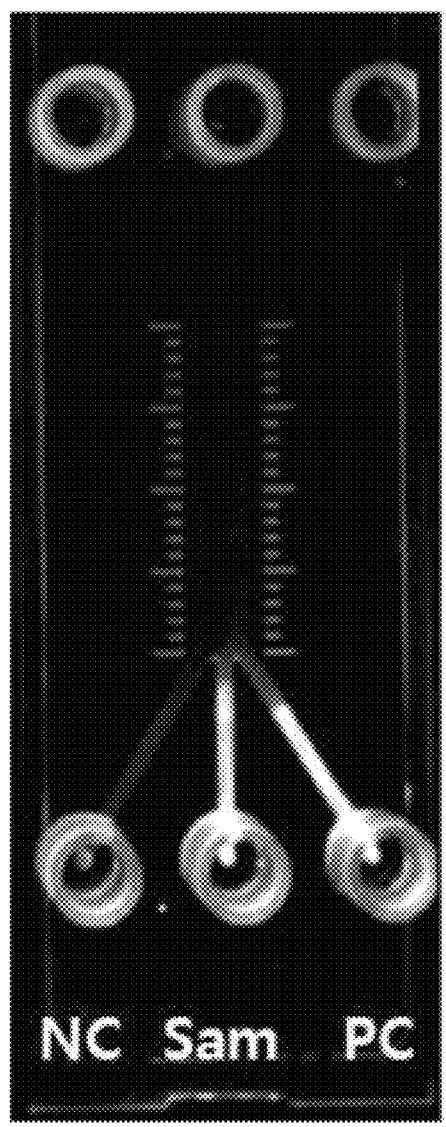
FIG. 14 shows a result of detecting MERS virus using a microfluidic device for detecting a target MERS gene.

The result is illustrated in FIG. 14. In FIG. 14, the outlet of the right second channel as the NC was not blocked, so that the sample flowed out. RCA occurred in the middle second channel as the sample and the right second channel as the PC to form hydrogel mass, which blocked the outlets.

DESCRIPTION OF REFERENCE NUMERALS

100: board
101: inlet
102: first channel
103: second channel
104: outlet

The invention claimed is:

1. A microfluidic device for detecting a target gene comprising:
- a board;
- an inlet which is formed on the board and through which a sample solution is introduced from outside the microfluidic device;
- a first channel connected to the inlet to accommodate the introduced sample solution;
- a second channel connected to the first channel;
- an outlet connected to the second channel;
- a surface coating on the second channel;
- a primer immobilized on the surface coating of the second channel; and
- a template complementarily binding to the primer,
- wherein: (a) the template is SEQ ID NO:1, SEQ ID NO:2, SEQ ID NO:3, SEQ ID NO:4, SEQ ID NO:10, SEQ ID NO:11 or SEQ ID NO:16, (b) the template comprises target binding regions complementary to a target gene, a primer binding region complementary to the primer, and in-template complementary binding regions, (c) the target binding regions complementary to the target gene are separately located at both ends of the template, (d) the primer binding region complementary to the primer is located between the in-template complementary binding regions, (e) a first one of the in-template complementary binding regions is located between the primer binding region and a first one of the target binding regions, (f) a second one of the in-template complementary binding regions is located between the primer binding region and a second one of the target binding regions, and (g) the in-template complementary binding regions are configured to complementarily bind to each other to form the dumbbell shape.

2. The microfluidic device of claim 1, wherein the second channel comprises 1 to 20 channels.

3. The microfluidic device of claim 1, wherein the second channel comprises 1 to 20 channels, which diverge from an end of the first channel, and the template complementarily binding to the primer immobilized on the surface coating of each second channel binds to the same or a different target gene.

4. The microfluidic device of claim 1, wherein the second channel is surface-coated with at least one member selected from the group consisting of 5-hydroxydopamine HCl, norepinephrine, epinephrine, pyrogallol amine, 3,4-Dihydroxyphenylalanine, catechin, tannins, pyrogallol, pyrocatechol, heparin-catechol, chitosan-catechol, poly(ethylene glycol)-catechol, poly(ethyleneimine)-catechol, poly(methyl methacrylate)-catechol, hyaluronic acid-catechol, polylysine-catechol, and polylysine.

5. The microfluidic device of claim 1, wherein the primer has an end modified with at least one member selected from the group consisting of thiol, amine, hydroxyl, carboxyl, isothiocyanate, NHS ester, aldehyde, epoxide, carbonate, HOBt ester, glutaraldehyde, carbamate, imidazole carbamate, maleimide, aziridine, sulfone, vinylsulfone, hydrazine, phenyl azide, benzophenone, anthraquinone, and diene.

6. The microfluidic device of claim 1, wherein the surface coating comprises 5-hydroxydopamine HCl, and the primer has an end modified with a thiol group or an amine group.

7. The microfluidic device of claim 1, wherein the target gene is derived from at least one member selected from the group consisting of avian influenza, SARS, *Escherichia coli* O157:H7, *Mycobacterium tuberculosis*, *Bacillus anthracis*, *Streptococcus pneumonia*, *Plasmodium*, *Salmonella*, Hepatitis A, B, C, D and E virus, *Francisella tularensis*, *Yersinia pestis*, *Yersinia enterocolitica*, Ebola virus, and MERS-Cov virus.

8. A microfluidic device kit for detecting a target gene comprising:
- the microfluidic device for detecting the target gene of claim 1;
- a dNTP;
- a ligase; and
- an isothermal nucleic acid polymerase.

9. The microfluidic device kit of claim 8, wherein the ligase is a DNA ligase, and the isothermal nucleic acid polymerase is phi29 polymerase.

10. The microfluidic device kit of claim 8, further comprising a dye reagent, a high salt solution, or a fluorescent reagent.

11. A method for manufacturing the microfluidic device for detecting a target gene according to claim 1 comprising:
- (S1) providing a microfluidic device comprising a board, an inlet which is formed on the board and through which a sample solution is introduced from outside the microfluidic device, a first channel connected to the inlet to accommodate the introduced sample solution, a second channel connected to the first channel, and an outlet connected to the second channel;
- (S2) coating the second channel of the microfluidic device to provide a coated second channel;
- (S3) immobilizing a primer to bind to a template on the coated second channel; and
- (S4) binding, to the primer, a template comprising the target binding regions complementary to a target gene, the primer binding region complementary to the primer, and the in-template complementary binding regions,
- wherein: (a) the target binding regions complementary to the target gene are separately formed at both ends of the template, (b) the primer binding region complementary to the primer is formed between the in-template complementary binding regions, (c) the first one of the in-template complementary binding regions is located between the primer binding region and the first, one of the target binding regions, (d) the second one of the in-template complementary binding regions is located between the primer binding region and the second one of the target binding regions, and (e) the in-template complementary binding regions are configured to complementarily bind to each other to form the dumbbell shape.

12. A method for detecting a target gene using the microfluidic device for detecting the target gene of claim 1 comprising:
   (S1) providing the microfluidic device for detecting the target gene of claim 1;
   (S2) introducing a sample solution into the first channel; and
   (S3) adding a dNTP, a ligase, and an isothermal nucleic acid polymerase to the second channel of the microfluidic device for detecting the target gene.

13. The method of claim 12, comprising (S4) allowing amplified gene products to flocculate to form hydrogel with a diameter of 50 μm to 5 mm on the second channel and an outlet.

14. The method of claim 13, further comprising (S5) adding a dye reagent, a high salt solution, or a fluorescent reagent.

* * * * *

SEQUENCE LISTING

```
<160> NUMBER OF SEQ ID NOS: 17

<210> SEQ ID NO 1
<211> LENGTH: 108
<212> TYPE: DNA
<213> ORGANISM: Artificial Sequence
<220> FEATURE:
<223> OTHER INFORMATION: Template specific for Salmonella
<220> FEATURE:
<221> NAME/KEY: modified_base
<222> LOCATION: (1)..(1)
<223> OTHER INFORMATION: 5'OH group of t is substituted with phosphate
      group

<400> SEQUENCE: 1
tgctatgccg actcaatcga agtactcagc gtaagtttag aggcattagc atgctagtat      60
cgacgtccca cgtaccaaca acttacgctg agtacttcga tttgagtg                  108

<210> SEQ ID NO 2
<211> LENGTH: 110
<212> TYPE: DNA
<213> ORGANISM: Artificial Sequence
<220> FEATURE:
<223> OTHER INFORMATION: Template specific for Yersinia enterocolitica
<220> FEATURE:
<221> NAME/KEY: modified_base
<222> LOCATION: (1)..(1)
<223> OTHER INFORMATION: 5'OH group of g is substituted with phosphate
      group

<400> SEQUENCE: 2
gctcacccca gtaaaatcga agtactcagc gtaagtttag aggcattagc atgctagtat      60
cgacgtccca cgtaccaaca acttacgctg agtacttcga ttagctttac                110

<210> SEQ ID NO 3
<211> LENGTH: 112
<212> TYPE: DNA
<213> ORGANISM: Artificial Sequence
<220> FEATURE:
<223> OTHER INFORMATION: Template specific for Francisella tularensis
<220> FEATURE:
<221> NAME/KEY: modified_base
<222> LOCATION: (1)..(1)
<223> OTHER INFORMATION: 5'OH group of t is substituted with phosphate
      group
```

<400> SEQUENCE: 3
tgtttccagt atttaatcga agtactcagc gtaagtttag aggcattagc atgctagtat    60
cgacgtccca cgtaccaaca acttacgctg agtacttcga ttttttcctcc ga          112

<210> SEQ ID NO 4
<211> LENGTH: 111
<212> TYPE: DNA
<213> ORGANISM: Artificial Sequence
<220> FEATURE:
<223> OTHER INFORMATION: Template specific for Yersinia pestis
<220> FEATURE:
<221> NAME/KEY: modified_base
<222> LOCATION: (1)..(1)
<223> OTHER INFORMATION: 5'OH group of t is substituted with phosphate
      group

<400> SEQUENCE: 4
tcgaatgcca acaaaatcga agtactcagc gtaagtttag aggcattagc atgctagtat    60
cgacgtccca cgtaccaaca acttacgctg agtacttcga ttctctgaac a             111

<210> SEQ ID NO 5
<211> LENGTH: 20
<212> TYPE: DNA
<213> ORGANISM: Artificial Sequence
<220> FEATURE:
<223> OTHER INFORMATION: Salmonella sequence which binds to template
      specific for Salmonella
<220> FEATURE:
<221> NAME/KEY: modified_base
<222> LOCATION: (20)..(20)
<223> OTHER INFORMATION: 3'OH group of a is substituted with phosphate
      group

<400> SEQUENCE: 5
gagtcggcat agcacactca                                                 20

<210> SEQ ID NO 6
<211> LENGTH: 22
<212> TYPE: DNA
<213> ORGANISM: Artificial Sequence
<220> FEATURE:
<223> OTHER INFORMATION: Yersinia enterocolitica sequence which binds to
      template specific for Yersinia enterocolitica
<220> FEATURE:
<221> NAME/KEY: modified_base
<222> LOCATION: (22)..(22)
<223> OTHER INFORMATION: 3'OH group of t is substituted with phosphate
      group

<400> SEQUENCE: 6
ttactggggt gagcgtaaag ct                                              22

<210> SEQ ID NO 7
<211> LENGTH: 24
<212> TYPE: DNA
<213> ORGANISM: Artificial Sequence
<220> FEATURE:
<223> OTHER INFORMATION: Francisella tularensis sequence which binds to
      template specific for Francisella tularensis
<220> FEATURE:
<221> NAME/KEY: modified_base
<222> LOCATION: (24)..(24)
<223> OTHER INFORMATION: 3'OH group of a is substituted with phosphate
      group

<400> SEQUENCE: 7
aaatactgga aacatcggag gaaa                                            24

<210> SEQ ID NO 8
<211> LENGTH: 23
<212> TYPE: DNA
<213> ORGANISM: Artificial Sequence
<220> FEATURE:
<223> OTHER INFORMATION: Yersinia pestis sequence which binds to
    template specific for Yersinia pestis
<220> FEATURE:
<221> NAME/KEY: modified_base
<222> LOCATION: (23)..(23)
<223> OTHER INFORMATION: 3'OH group of g is substituted with phosphate group

<400> SEQUENCE: 8
ttgttggcat tcgatgttca gag 23

<210> SEQ ID NO 9
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: a is modified with the thiol group

<400> SEQUENCE: 9
aaaaaaaaag ggacgtcgat actagcatgc ta 32

<210> SEQ ID NO 10
<211> LENGTH: 99
<212> TYPE: DNA
<213> ORGANISM: Artificial Sequence
<220> FEATURE:
<223> OTHER INFORMATION: Template specific for Bacillus anthracis
<220> FEATURE:
<221> NAME/KEY: modified_base
<222> LOCATION: (1)..(1)
<223> OTHER INFORMATION: 5'OH group of t is substituted with phosphate group

<400> SEQUENCE: 10
tttgaaatgg agaaaatcga agtactcagc gtaagtttag aggtagcatg ctagtatcga 60
cgtacgtacc aacttacgct gagtacttcg atttgagcg 99

<210> SEQ ID NO 11
<211> LENGTH: 104
<212> TYPE: DNA
<213> ORGANISM: Artificial Sequence
<220> FEATURE:
<223> OTHER INFORMATION: Template specific for Ebola virus
<220> FEATURE:
<221> NAME/KEY: modified_base
<222> LOCATION: (1)..(1)
<223> OTHER INFORMATION: 5'OH group of g is substituted with phosphate group

<400> SEQUENCE: 11
gacgcacgcg aatcgaagta ctcagcgtaa gtttagaggt agcatgctag tatcgacgta 60
cgtaccaact tacgctgagt acttcgatta acgagaaatc gcac 104

<210> SEQ ID NO 12
<211> LENGTH: 20
<212> TYPE: DNA
<213> ORGANISM: Artificial Sequence
<220> FEATURE:
<223> OTHER INFORMATION: Bacillus anthracis sequence which binds to template specific for Bacillus anthracis
<220> FEATURE:
<221> NAME/KEY: modified_base
<222> LOCATION: (20)..(20)
<223> OTHER INFORMATION: 3'OH group of a is substituted with phosphate
      group

<400> SEQUENCE: 12
ttctccattt caaacgctca                                              20

<210> SEQ ID NO 13
<211> LENGTH: 25
<212> TYPE: DNA
<213> ORGANISM: Artificial Sequence
<220> FEATURE:
<223> OTHER INFORMATION: Ebola virus sequence which binds to template
      specific for Ebola virus
<220> FEATURE:
<221> NAME/KEY: modified_base
<222> LOCATION: (25)..(25)
<223> OTHER INFORMATION: 3'OH group of t is substituted with phosphate
      group

<400> SEQUENCE: 13
cgcgtgcgtc gtgcgatttc tcgtt                                        25

<210> SEQ ID NO 14
<211> LENGTH: 20
<212> TYPE: DNA
<213> ORGANISM: Artificial Sequence
<220> FEATURE:
<223> OTHER INFORMATION: Bacillus anthracis sequence which binds to
      template specific for Bacillus anthracis
<220> FEATURE:
<221> NAME/KEY: modified_base
<222> LOCATION: (20)..(20)

<400> SEQUENCE: 14
ttctccattt caaacgctca                                              20

<210> SEQ ID NO 15
<211> LENGTH: 25
<212> TYPE: DNA
<213> ORGANISM: Artificial Sequence
<220> FEATURE:
<223> OTHER INFORMATION: Ebola virus sequence which binds to template
      specific for Ebola virus
<220> FEATURE:
<221> NAME/KEY: modified_base
<222> LOCATION: (25)..(25)

<400> SEQUENCE: 15
cgcgtgcgtc gtgcgatttc tcgtt                                        25

<210> SEQ ID NO 16
<211> LENGTH: 99
<212> TYPE: DNA
<213> ORGANISM: Artificial Sequence
<220> FEATURE:
<223> OTHER INFORMATION: Template specific for MER-Corona Virus

<400> SEQUENCE: 16
agggcacatc tccgaatcga agtactcagc gtaagtttag aggtagcatg ctagtatcga    60
cgtacgtacc aacttacgct gagtacttcg attataccc                          99

<210> SEQ ID NO 17
<211> LENGTH: 20
<212> TYPE: DNA

```
<213> ORGANISM: Artificial Sequence
<220> FEATURE:
<223> OTHER INFORMATION: MERS-Corona Virus sequence which binds to
      template specific for MERS-Corona Virus

<400> SEQUENCE: 17
cggagaugug cccuggguau                                                20
```